(12) United States Patent
Lee et al.

(10) Patent No.: US 9,539,391 B2
(45) Date of Patent: *Jan. 10, 2017

(54) METHODS AND DEVICES FOR AUTOFLUSH SYRINGES

(71) Applicant: Shi Zi Technology, Ltd., Cybercity, Ebene (MU)

(72) Inventors: Martin N. Lee, Baltimore, MD (US); Jeffrey J. Christian, Morgan Hill, CA (US); Michael D. Laufer, Menlo Park, CA (US); Geoffrey H. Willis, Campbell, CA (US)

(73) Assignee: Shi Zi Technology, Ltd., Ebene (MU)

( * ) Notice: Subject to any disclaimer, the term of this patent is extended or adjusted under 35 U.S.C. 154(b) by 0 days.

This patent is subject to a terminal disclaimer.

(21) Appl. No.: 14/597,097

(22) Filed: Jan. 14, 2015

(65) Prior Publication Data

US 2015/0190576 A1 Jul. 9, 2015

Related U.S. Application Data

(63) Continuation of application No. 13/356,477, filed on Jan. 23, 2012, now Pat. No. 8,936,577, which is a
(Continued)

(51) Int. Cl.
*A61M 5/19* (2006.01)
*A61M 5/31* (2006.01)
(Continued)

(52) U.S. Cl.
CPC ........... *A61M 5/19* (2013.01); *A61M 5/31596* (2013.01); *A61M 5/315* (2013.01); *A61M 5/3129* (2013.01);
(Continued)

(58) Field of Classification Search
CPC ................. A61M 2005/1787; A61M 5/31596; A61M 5/3129; A61M 5/19; A61M 5/3146; A61M 5/31511; A61M 5/502; A61M 5/315; A61M 2005/3106; A61M 2005/3123; A61M 2005/3128; A61M 2005/31508; A61M 2005/31598; A61M 2205/583
See application file for complete search history.

(56) References Cited

U.S. PATENT DOCUMENTS

| 368,627 A | 8/1887 | Threlfall |
| 553,234 A | 1/1896 | Finot |

(Continued)

FOREIGN PATENT DOCUMENTS

| WO | WO 98/05433 | 2/1998 |
| WO | WO 2006/118949 | 11/2006 |

(Continued)

*Primary Examiner* — Theodore Stigell
(74) *Attorney, Agent, or Firm* — Levine Bagade Han LLP

(57) ABSTRACT

Described herein are syringe devices, systems and methods. In general, the syringe may include a first chamber and a cartridge movable within the first chamber. The cartridge may include a cartridge chamber and a valve in fluid communication with the cartridge chamber and the first chamber and having an open configuration and a closed configuration. The valve may allow movement of a liquid out of the cartridge chamber while in a open configuration. The cartridge may also include a second end, movable within the cartridge chamber, and a locking mechanism having a locked configuration and an unlocked configuration, the locking mechanism preventing movement of the second end within the cartridge chamber while in the locked configuration.

8 Claims, 26 Drawing Sheets

Related U.S. Application Data continuation-in-part of application No. 12/847,825, filed on Jul. 30, 2010, now abandoned, and a continuation-in-part of application No. 12/833,735, filed on Jul. 9, 2010, now Pat. No. 8,529,517, which is a continuation-in-part of application No. 11/120,906, filed on May 2, 2005, now Pat. No. 8,075,533.

(51) Int. Cl.
　　*A61M 5/315*　　(2006.01)
　　*A61M 5/50*　　(2006.01)
　　*A61M 5/178*　　(2006.01)

(52) U.S. Cl.
　　CPC ......... *A61M 5/3146* (2013.01); *A61M 5/31511* (2013.01); *A61M 5/502* (2013.01); *A61M 2005/1787* (2013.01); *A61M 2005/3106* (2013.01); *A61M 2005/3123* (2013.01); *A61M 2005/3128* (2013.01); *A61M 2005/31508* (2013.01); *A61M 2005/31598* (2013.01); *A61M 2205/583* (2013.01)

(56) References Cited

U.S. PATENT DOCUMENTS

| | | |
|---|---|---|
| 1,142,682 A | 6/1915 | Dickinson |
| 1,234,582 A | 7/1917 | Trueblood |
| 1,343,787 A | 6/1920 | Ewell |
| 2,841,145 A | 7/1958 | Epps |
| 3,487,834 A | 1/1970 | Smith, Jr. et al. |
| 3,559,645 A | 2/1971 | Schaller |
| 3,605,742 A | 9/1971 | Tibbs |
| 3,705,582 A | 12/1972 | Stumpf et al. |
| 3,729,031 A | 4/1973 | Baldwin |
| 3,747,812 A | 7/1973 | Karman et al. |
| 3,826,260 A | 7/1974 | Killinger |
| 3,835,835 A | 9/1974 | Thompson et al. |
| 3,923,058 A | 12/1975 | Weingarten |
| 4,171,698 A | 10/1979 | Genese |
| 4,188,949 A | 2/1980 | Antoshkiw |
| 4,313,439 A | 2/1982 | Babb et al. |
| 4,411,157 A | 10/1983 | Babin et al. |
| 4,425,120 A | 1/1984 | Sampson et al. |
| 4,452,473 A | 6/1984 | Ruschke |
| 4,476,866 A | 10/1984 | Chin |
| 4,501,306 A | 2/1985 | Chu et al. |
| 4,506,691 A | 3/1985 | Tseo |
| 4,562,844 A | 1/1986 | Carpenter et al. |
| 4,581,015 A | 4/1986 | Alfano |
| 4,583,978 A | 4/1986 | Porat et al. |
| 4,655,747 A | 4/1987 | Allen, Jr. |
| 4,685,910 A | 8/1987 | Schweizer |
| 4,693,706 A | 9/1987 | Ennis, III |
| 4,702,737 A | 10/1987 | Pizzino |
| 4,702,738 A | 10/1987 | Spencer |
| 4,715,853 A | 12/1987 | Prindle |
| 4,723,943 A | 2/1988 | Spencer |
| 4,737,144 A | 4/1988 | Choksi |
| 4,747,834 A | 5/1988 | Prindle |
| 4,758,232 A | 7/1988 | Chak |
| 4,871,353 A | 10/1989 | Thomsen |
| 4,874,385 A | 10/1989 | Moran et al. |
| 4,929,230 A | 5/1990 | Pfleger |
| 4,929,238 A | 5/1990 | Baum |
| 4,950,241 A | 8/1990 | Ranford |
| 4,986,813 A | 1/1991 | Blake, III et al. |
| 4,988,339 A | 1/1991 | Vadher |
| 4,994,045 A | 2/1991 | Ranford |
| 5,032,117 A | 7/1991 | Motta |
| 5,061,252 A | 10/1991 | Dragosits |
| 5,067,948 A | 11/1991 | Haber et al. |
| 5,137,521 A | 8/1992 | Wilkins |
| 5,176,635 A | 1/1993 | Dittmann |
| 5,358,497 A | 10/1994 | Dorsey et al. |
| 5,374,250 A | 12/1994 | Dixon |
| 5,435,076 A | 7/1995 | Hjertman et al. |
| 5,496,284 A | 3/1996 | Waldenburg |
| 5,512,054 A | 4/1996 | Morningstar |
| 5,688,250 A | 11/1997 | Naganuma |
| 5,713,873 A | 2/1998 | Jehle |
| 5,720,731 A | 2/1998 | Aramata et al. |
| 5,772,433 A | 6/1998 | Esrock |
| 5,772,630 A | 6/1998 | Ljungquist |
| 5,833,654 A | 11/1998 | Powers et al. |
| 5,875,976 A | 3/1999 | Nelson et al. |
| 6,090,077 A | 7/2000 | Shaw |
| 6,093,170 A | 7/2000 | Hsu et al. |
| 6,270,482 B1 | 8/2001 | Rosoff et al. |
| 6,361,524 B1 | 3/2002 | Odell et al. |
| 6,423,050 B1 | 7/2002 | Twardowski |
| 6,558,358 B2 | 5/2003 | Rosoff et al. |
| 6,719,733 B1 | 4/2004 | Heffernan et al. |
| 6,723,074 B1 | 4/2004 | Halseth |
| 6,780,167 B2 | 8/2004 | Leone |
| 8,075,533 B2 * | 12/2011 | Lee .................. A61M 5/31596 604/191 |
| 8,075,547 B2 * | 12/2011 | Lee .................. A61M 5/31596 604/191 |
| 8,529,517 B2 * | 9/2013 | Lee .................. A61M 5/31596 604/191 |
| 8,936,577 B2 * | 1/2015 | Lee .................. A61M 5/31596 604/191 |
| 2012/0029471 A1 | 2/2012 | Lee et al. |
| 2012/0197232 A1 | 8/2012 | Lee et al. |

FOREIGN PATENT DOCUMENTS

| | | |
|---|---|---|
| WO | WO 2009/094345 | 7/2009 |
| WO | WO 2011/014259 | 2/2011 |
| WO | WO 2011/055243 | 5/2011 |
| WO | WO 2012/006555 | 1/2012 |

\* cited by examiner

FIG. 1
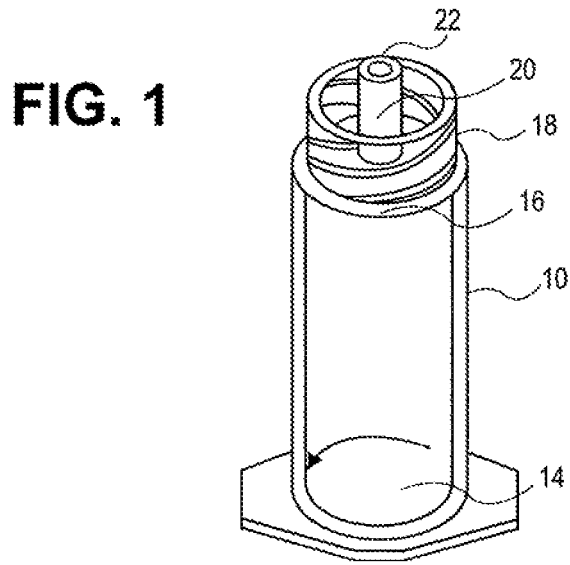
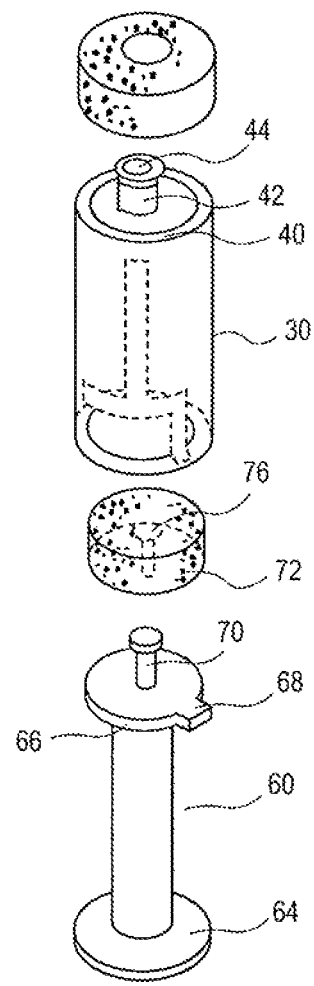

FIG. 2
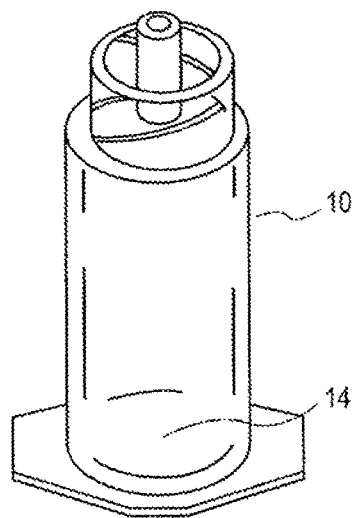
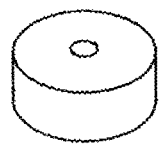
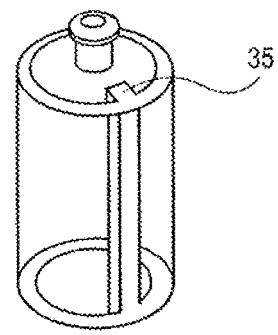
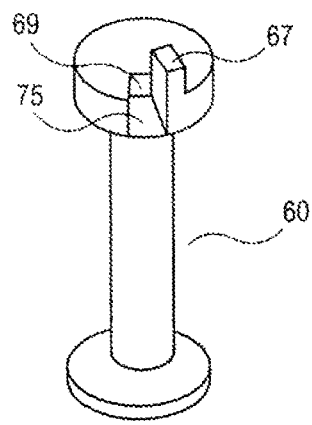

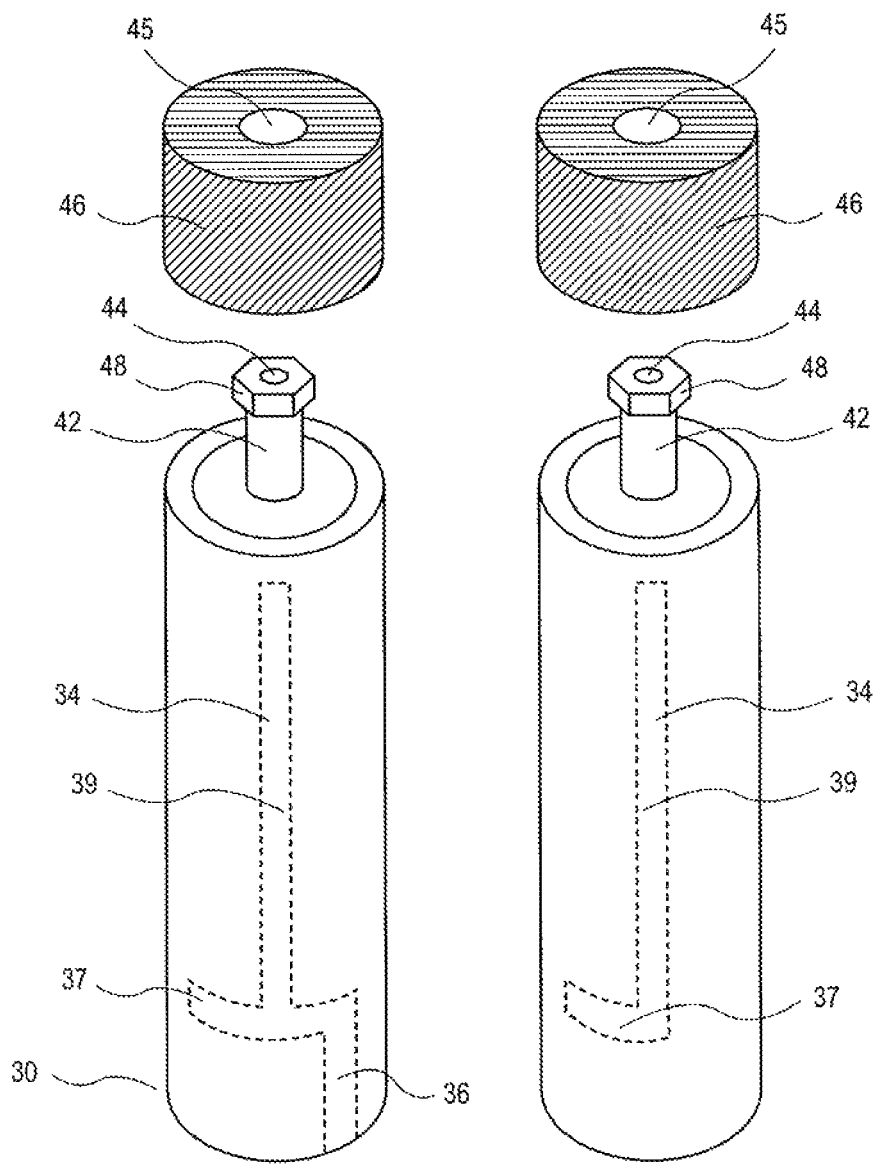

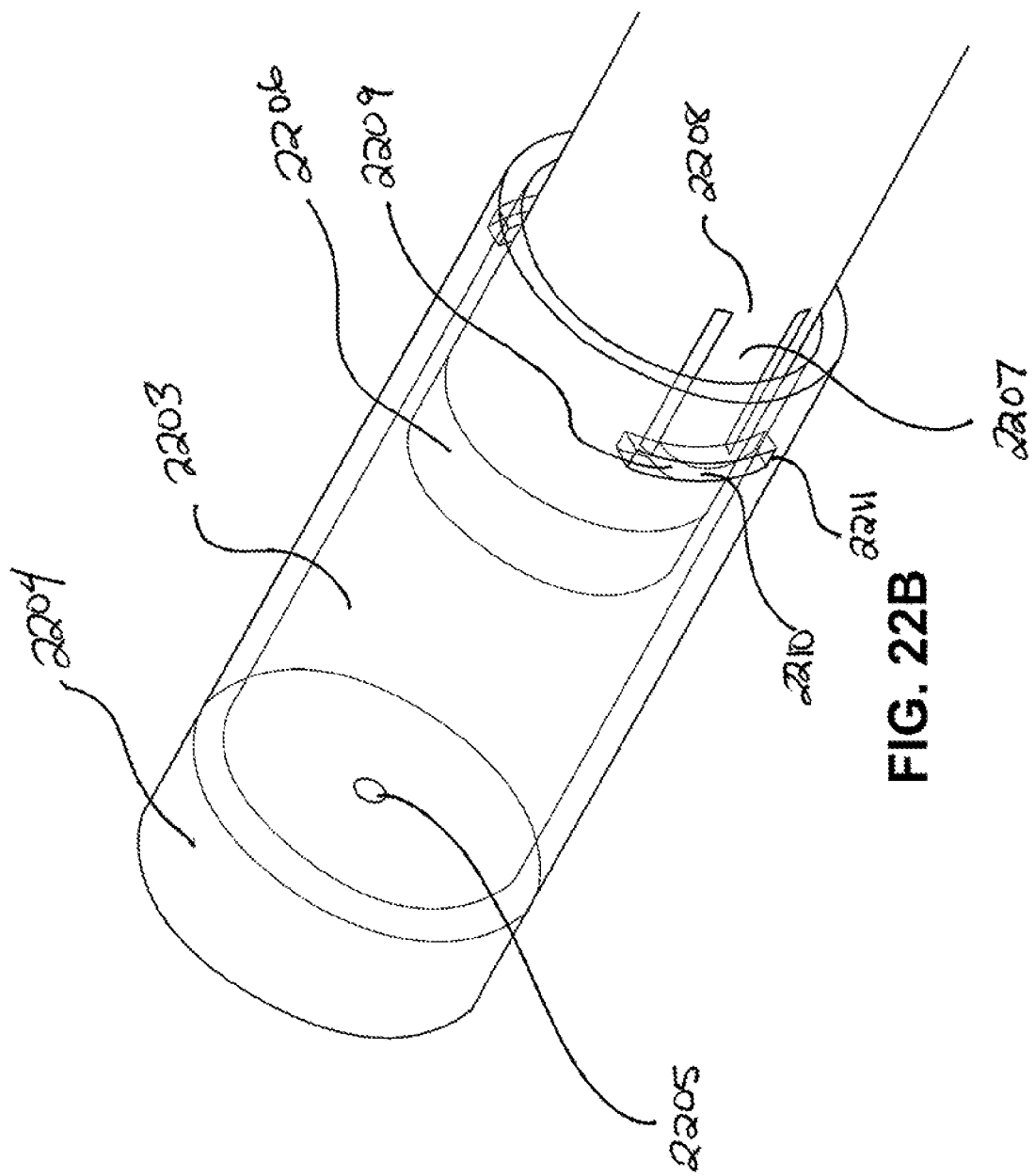

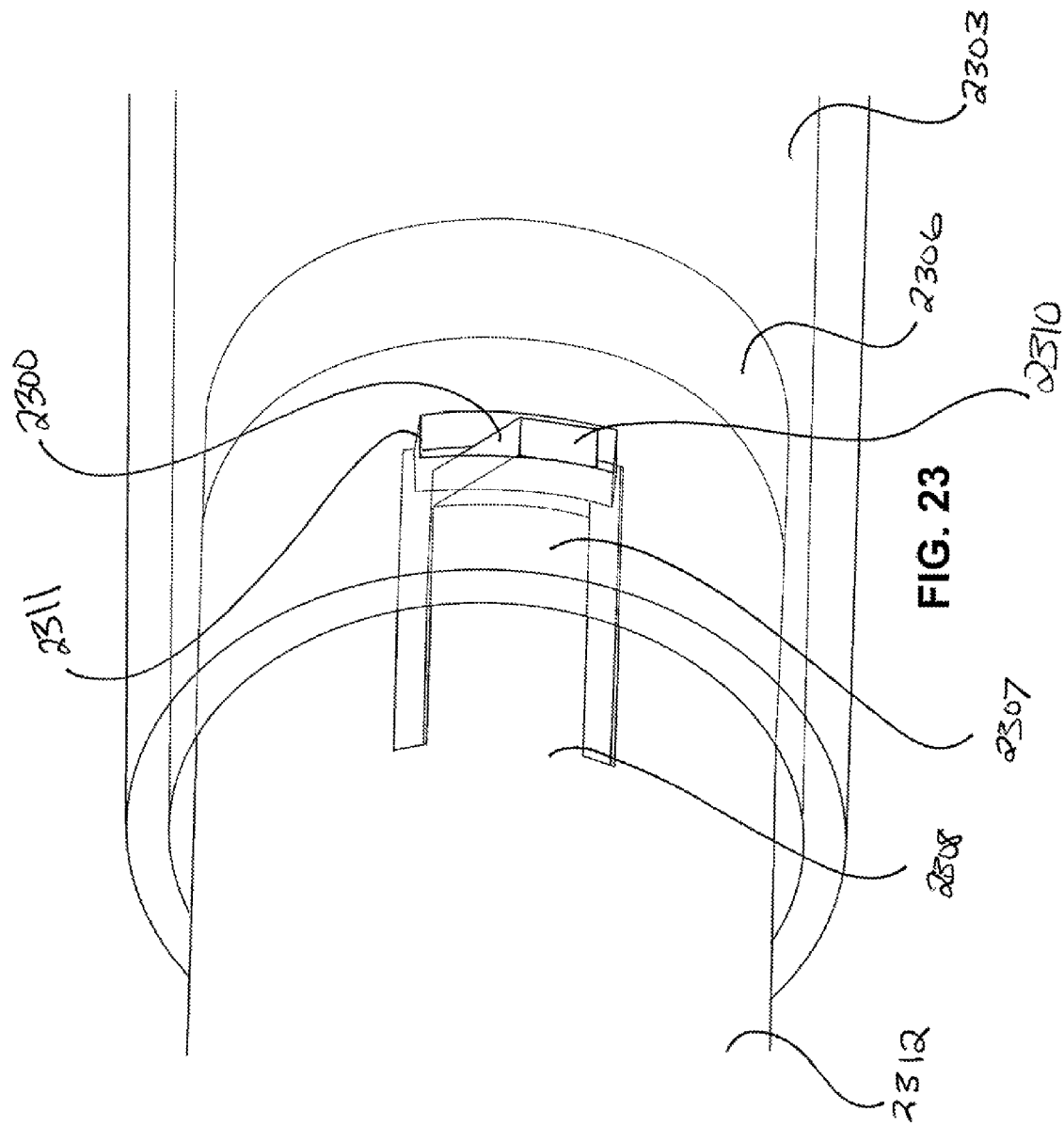

METHODS AND DEVICES FOR AUTOFLUSH SYRINGES

CROSS-REFERENCE TO RELATED APPLICATIONS

This application is a continuation of U.S. patent application Ser. No. 13/356,477, filed Jan. 23, 2012 (now U.S. Pat. No. 8,936,577), which is a continuation in part of U.S. patent application Ser. No. 12/847,825, filed Jul. 30, 2010 and is a continuation in part of U.S. patent application Ser. No. 12/833,735, filed Jul. 9, 2010 (now U.S. Pat. No. 8,529,517, issued Sep. 10, 2013), which is a continuation in part of U.S. patent application Ser. No. 11/120,906, filed May 2, 2005, (now U.S. Pat. No. 8,075,533, issued Dec. 13, 2011), the contents each of which are incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

1. Field of the Invention

This invention relates to syringe injectors.

2. General Background

Syringes are commonly used in the medical field for the injection or withdrawal of liquid medications. Syringes typically have a hollow glass or plastic barrel with an internal piston. By moving the piston, a user can create a positive or negative pressure inside the barrel, thereby transmitting fluid out of or into the barrel through a small opening opposite the piston.

Syringes are often used in intravenous therapy where the syringe may directly puncture the vein, or more commonly, may be used in conjunction with a catheter. When a catheter is used, one side of the catheter remains in the vein, while the other side remains outside the skin. The external portion of the catheter typically includes a coupler for connection to a syringe.

After injection in either procedure, a small amount of medication is typically left behind. When a syringe is used, the medication remains within the tip of the syringe. When a catheter is used in conjunction with a syringe, the unadministered medication remains in the both the tip of the syringe and in the catheter.

This leftover medication is problematic for several reasons. First, it necessarily means that the entire amount of medicine drawn into the syringe does not reach the patient. Second, many medications are time sensitive and should not remain in the catheter until a subsequent medicine flushes it through.

In a catheter system, these problems are solved using a second liquid to immediately flush the remaining medication out of the catheter and into the patient. Generally, a second syringe prefilled with a flushing solution provides the second liquid.

While many different liquids may be used to flush the catheter, the most commonly used liquid is a 0.9% concentration of sodium chloride (saline solution). The saline solution is injected from a syringe into the catheter, thereby flushing any stranded medication into the patient. Thus, the saline flush ensures that a full dosage of medication has been timely delivered.

This method for purging the catheter has certain disadvantages. For instance, by using a separate syringe for each injection, there is an increased chance of medical error. Most medicines are colorless (like the saline solution), and it is easy to accidentally administer medication when intending to flush the line or vice versa. This risk is increased when clinicians carry medicines for multiple patients at one time.

The likelihood of error is compounded in an emergency, when it may be necessary to inject several medications quickly and in a specific order. In such situations, a separate saline flush is necessary between every individual medication injection, so the risk of error is high, and the consequences of a mistake may be grave.

Finally, the clinician may be distracted by a separate medical need during the time between the injection of medication and the saline flush. Without some reminder, the clinician may forget that he or she has not flushed the line.

Even if all precautions are taken and the two injections are made in the proper order, drawbacks remain. With each breach of the catheter's seal for injection, the patient is potentially exposed to bacteria, increasing the risk of infection. By requiring a clinician to access the system once for the medication and a second time for the flush, the risk of infection is doubled.

Using a second syringe for the saline flush also wastes resources. Attaching a second syringe to the catheter takes time, and since a clinician may perform a saline flush more than one hundred times per day, this lost time adds up quickly. Finally, requiring a second syringe unnecessarily increases the already significant costs related to manufacturing, shipping, storage, and disposal of syringes.

Previous attempts to provide syringes adapted to deliver multiple fluids for sequential injection can be found in various patents discussed herein. Some conventional syringes include a "standard" syringe that is separated by an intermediate sliding stopper into two chambers. The sliding stopper receives motive force communicated through an intermediate fluid from a primary stopper (part of a plunger assembly of the standard syringe) against which an external force is applied. Examples of such prior art devices may be found in U.S. Pat. Nos. 6,997,910 and 7,101,354 which describe multiple embodiments of a conventional syringe adapted to deliver multiple fluids and a displaceable valved stopper which partitions a conventional syringe.

There are several disadvantages associated with the previously described syringes adapted to deliver multiple fluids. These include: reliance on the intermediate fluid in the proximal chamber to transmit the force from the plunger to the sliding stopper to expel the primary fluid; the absence of a physical locking mechanism to prevent the intermediate fluid from being expelled accidentally due to increased pressure; the need for a filling procedure that includes placing the intermediate sliding stopper into the syringe barrel, then backfilling with a liquid and subsequently installing the plunger assembly and therefore relying on the compressibility of the gas trapped in the proximal chamber for a successful installation of the plunger; prefilled proximal and distal chambers that force the caregiver away from their standard syringe filling procedures; and a limit to the volume of medicine that can be filled into the distal chamber caused by the presence of the filled proximal chamber.

The devices and methods described in the present application provide improved means for delivering multiple fluids sequentially. Moreover, variations of the devices and methods described herein can optionally include a simple design that makes storage easy and keeps manufacturing costs to a minimum. In an additional variation, the devices and methods does not rely on the fluid in the proximal chamber to expel the primary fluid (medicine) from the syringe. Instead, the methods and devices described in the present disclosure rely upon the presence of a fluid (typically air) gap to maintain separation of fluids until desired. Variations of the present methods and devices can include a physical locking mechanism such that the intermediate fluid cannot be expelled accidentally due to increased pressure; it allows filling of the proximal chamber from the distal end (during manufacturing), which enables complete filling of the proximal chamber without trapping any large/non injectable air bubbles, it allows caregivers to follow their standard syringe filling procedures; and it does not limit the volume of medicine that can be filled into the distal chamber. Any number of locking mechanisms is within the scope of this disclosure.

The present invention advances the state of the art by providing a cost-effective single syringe that both administers medication and flushes the intravenous system. By using a single syringe for both purposes, a clinician need only access the intravenous catheter once, thereby decreasing the rate of error and infection. Additionally, the presence of the saline or other solution in the syringe after injection alerts the clinician of the need to flush the system, thus reducing the chance that the flush would be forgotten. Finally, the extra cost and time associated with a second "flush-only" syringe would be eliminated.

SUMMARY OF THE INVENTION

The present invention is a two-chambered syringe with an outer barrel having an open end for slidably receiving an inner barrel/first piston. A second piston is slidably movable in the inner barrel/first piston. A latching mechanism locks and unlocks the inner barrel/first piston to the second piston. In the locked configuration, the second piston is prevented from substantially all longitudinal movement relative to the inner barrel/first piston, and in the unlocked configuration, the second piston may move longitudinally within the inner barrel. Thus, the invention may be repeatedly used as a traditional syringe to withdraw medicine from a bottle, either before or after the administration of a second flushing solution contained in the syringe.

Syringes should optionally provide a cost-effective single syringe that both administers medication and flushes the intravenous system. It is desirable to not rely on the fluid in the proximal chamber to expel the primary fluid (medicine) from the syringe; to include a physical locking mechanism such that the intermediate fluid cannot be expelled accidentally due to increased pressure; to allow filling of the proximal chamber from the distal end (during manufacturing), which enables complete filling of the proximal chamber without trapping any large/non injectable air bubbles; to allow caregivers to follow their standard syringe filling procedures; and to not limit the volume of medicine that can be filled into the distal chamber.

Described herein are syringe devices, systems and methods. In general, the syringe may include a first chamber and a cartridge movable within the first chamber. The cartridge may include a cartridge chamber and a valve in fluid communication with the cartridge chamber and the first chamber and having an open configuration and a closed configuration. The valve may allow movement of a liquid out of the cartridge chamber while in a open configuration. The cartridge may also include a second end, movable within the cartridge chamber, and a locking mechanism having a locked configuration and an unlocked configuration, the locking mechanism preventing movement of the second end within the cartridge chamber while in the locked configuration.

One aspect of the invention provides a syringe further includes a liquid disposed within the cartridge chamber. In some embodiments, the cartridge includes about 1 to 10 ml of liquid disposed within the cartridge chamber, while in some embodiments, the cartridge includes about 2 to 3 ml of liquid disposed within the cartridge chamber.

One variation of the device includes a syringe for dispensing a first liquid. For example such a syringe can include a first chamber having a moveable seal located therein such that movement of the moveable seal changes a volume of the first chamber, the first chamber having an outlet; a second chamber movable in the first chamber along with the first chamber movable seal, the second chamber comprising a second movable seal located therein such that movement of the second moveable seal changes a volume of the second chamber;

a second liquid located in the second chamber, where a volume of the second liquid at least fills the second chamber and a conduit fluidly connecting the first chamber and the second chamber where the conduit contains a fluid gap that is adjacent to the second liquid, where the conduit is configured to retain the fluid gap when the second liquid fills at least the volume of the second chamber, the fluid gap maintains the second liquid in the second chamber, where the fluid gap is retained in the conduit until the volume of the second chamber changes, such that while the volume of the second chamber remains unchanged volume of the first chamber can be altered by movement of the moveable seal without displacing the fluid gap.

The devices in the present disclosure can be fabricated from glass, a medical grade polymer, a metal, a metal alloy, or any material suitable for use in such applications.

Variations of the device can include a latching mechanism having a first position in which movement between the first chamber seal and the second chamber seal is prevented to maintain a volume of the second chamber at a fixed volume, and a second position in which movement between the first chamber seal and the second chamber seal is permitted. In an alternate variation, the lock or latching mechanism can simply comprise a resistance stop to oppose movement of the second movable seal. Such a resistance stop can prevent movement of the plunger until the second chamber bottoms out in the first.

Typically the fluid gap described herein comprises an air gap. However, other gasses can be used so long as they function to separate fluids from mixing as described herein.

The variations disclosed herein can include one or more valves located within the conduit. The valve can add an additional means of protection to avoid undesired mixture of fluids during storage and transportation of the syringe. In some embodiments, the syringe further includes a second liquid disposed within the first chamber, and the valve prevents movement of the second liquid into the cartridge chamber. However, the fluid gap remains the primary mechanism for separating the liquids in the respective chambers.

Variations of the invention also include methods for preparing a two-chambered syringe for sequential delivery of different liquids. In one example, the method includes positioning an opening of the syringe adjacent to a source of a secondary liquid where the syringe comprises a first chamber having a moveable seal located therein such that movement of the moveable seal changes a volume of the first chamber, the first chamber having an outlet, the syringe further comprising a second chamber movable in the first chamber along with the first chamber movable seal, the second chamber comprising a second movable seal located therein such that movement of the second moveable seal changes a volume of the second chamber, where the first and second chambers are fluidly coupled by a conduit; and filling the second chamber with the secondary liquid where a volume of the secondary liquid at least fills the second chamber leaving a fluid gap adjacent to the secondary liquid but within the conduit, where the conduit is configured to retain the fluid gap until displaced by a change in volume of the second chamber, such that while the volume of the second chamber remains unchanged the volume of the first chamber can be adjusted to draw in or expel a primary fluid through the opening without displacing the fluid gap.

Another variation of the method includes positioning an opening of the syringe adjacent to a source of a primary liquid where the syringe comprises a first chamber having a moveable seal located therein such that movement of the moveable seal changes a volume of the first chamber, the first chamber having an outlet, the syringe further comprising a second chamber movable in the first chamber along with the first chamber movable seal, the second chamber comprising a second movable seal located therein such that movement of the second moveable seal changes a volume of the second chamber, where the first and second chambers are fluidly coupled by a conduit; where the second chamber carries a secondary liquid that at least fills the second chamber and leaves a fluid gap within the conduit and adjacent to the secondary liquid, where the conduit is configured to retain the fluid gap until the volume of the second chamber changes; and drawing the primary liquid into the first chamber without changing a volume of the second chamber such that the primary fluid can be drawn into and expelled from the first chamber without displacing the fluid gap.

In some embodiments, the first end of the flexible arm is coupled to the second end of the cartridge and the groove is defined by the inner surface of the cartridge. In some embodiments, the flexible arm has an equilibrium configuration wherein the tab extends beyond the outer surface of the second end and a bent configuration wherein the tab does not extend beyond the outer surface of the second end. In some embodiments, the tab includes a ramped surface, such that when the second end is rotated within the inner surface of the cartridge, the ramped surface interacts with the groove such that the flexible arm is moved from the equilibrium configuration to the bent configuration. In some embodiments, the tab includes two ramped surfaces such that the second end may be rotated in two directions within the inner surface of the cartridge. In some embodiments, the locking mechanism is in the locked configuration when the flexible arm is in the equilibrium configuration and the tab is within the groove, and wherein the locking mechanism is in an unlocked configuration when the flexible arm is in the bent configuration and the tab is released from the groove. In some embodiments, the syringe further includes an adjacent groove adapted to receive the tab when the locking mechanism is in the unlocked configuration.

In some embodiments, the tab is substantially triangular shaped, while in some embodiments, the tab is substantially semi-circular shaped.

In some embodiments, the syringe further includes a second groove configured to receive the tab when the second end is in the second distal position. In some embodiments, the second groove extends around the circumference of the cartridge.

In some embodiments, the syringe further includes a first ridge on the inner surface of the cartridge, wherein the ridge is configured to prevent the withdrawal of the second end from the cartridge. In some embodiments, the syringe further includes a second ridge on the outer surface of the second end of the cartridge and a second ridge, wherein the ridges are configured to prevent the withdrawal of the second end from the cartridge.

In some embodiments, the cartridge further includes a first end that defines a channel in fluid communication with the cartridge chamber and the first chamber. In some embodiments, the first end of the cartridge is coupled to the first chamber, such that when the second end of the cartridge is rotated within the cartridge the first end is not rotated. In some embodiments, the first chamber has an oval cross section.

In some embodiments, the syringe further includes indicia that signify when the locking mechanism is in the locked configuration, and when the locking mechanism is in an unlocked configuration.

In some embodiments, the syringe further includes a ridge coupled to an end of the groove, wherein the ridge is configured to prevent the tab from reentering the groove after it has been released. In some embodiments, the second end of the cartridge further includes a handle sized and configured to move the second end within the cartridge. In some embodiments, the first end of the flexible arm is coupled to the handle.

In additional variations, the methods of using the syringe may include the steps of expelling a liquid from the first chamber through the outlet by moving the cartridge within the first chamber, increasing pressure within the cartridge chamber by moving the second end of the cartridge within the cartridge chamber, opening the valve with the increased pressure within the cartridge chamber, and expelling a second liquid from the cartridge chamber through the valve and through the outlet by further moving the second end of the cartridge within the cartridge chamber It should be understood that combinations of the various embodiments described herein or combinations of aspects of the embodiments themselves are within the scope of the disclosure.

BRIEF DESCRIPTION OF THE DRAWINGS

FIG. 1 is an exploded perspective view of a two-chambered syringe according to an embodiment of the present invention.

FIG. 2 is an exploded perspective view of a two-chambered syringe according to an embodiment of the present invention.

FIG. 7 is a perspective view of the inner barrel/first piston and sealing ring depicted in FIG. 1.

FIG. 8 is a perspective view of the inner barrel/first piston and sealing ring according to an alternative embodiment of the present invention.

FIGS. 22A-23 are perspective views of an embodiment of a syringe including a locking mechanism.

DETAILED DESCRIPTION OF THE INVENTION

Figure 3:
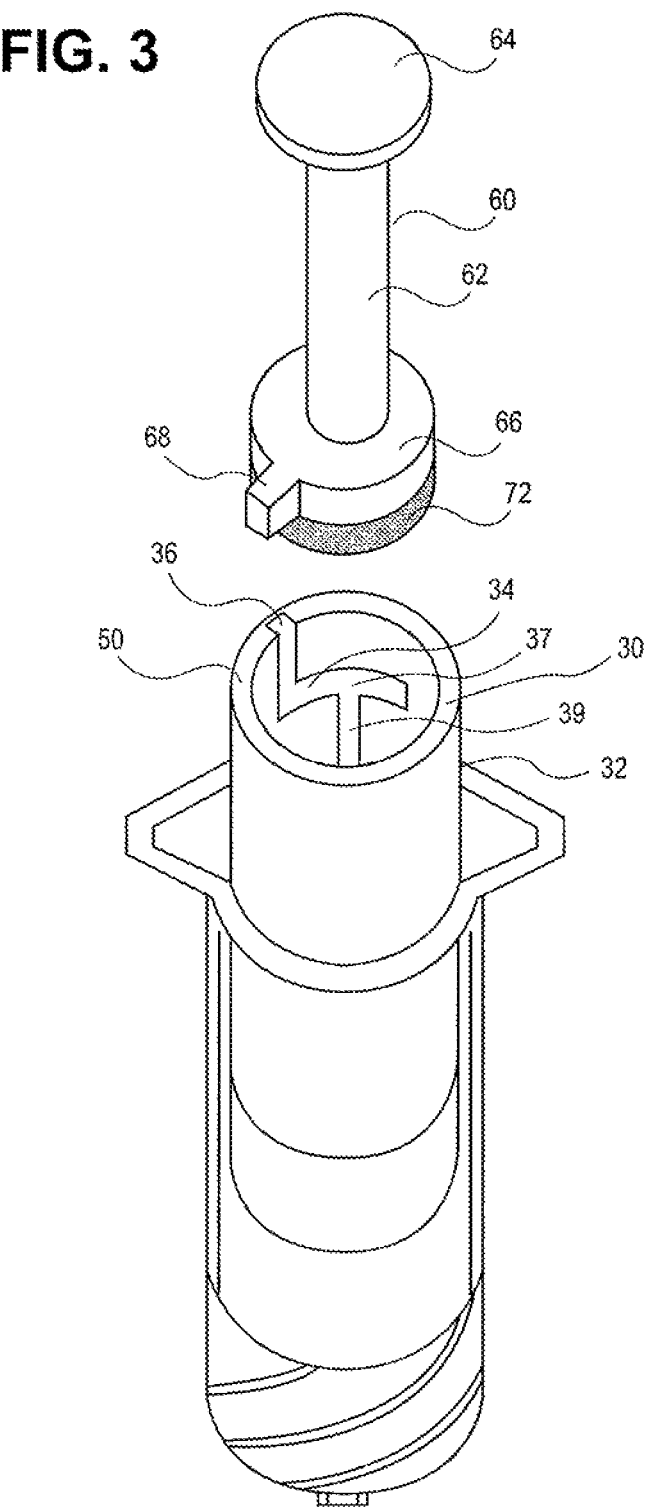
FIG. 3 is a perspective view of the embodiment depicted in FIG. 1.

Described herein are syringe devices, systems and methods. In general, the syringe may include a first chamber and a cartridge movable within the first chamber where construction of the chambers and conduits fluidly coupling the chambers allows for the maintenance of an air or fluid gap that serves to separate liquids or other substances in the various chambers. The air gap or fluid gap, described in detail below, provides the main mechanism to separate the fluids until the operator desires to eject or dispense the secondary or flush fluid.

Additional variations of the device can include a cartridge chamber and a valve in fluid communication with the cartridge chamber and the first chamber and having an open configuration and a closed configuration. The valve may allow movement of a liquid out of the cartridge chamber while in a open configuration. The cartridge may also include a second end movable within the cartridge chamber, and a locking mechanism having a locked configuration and an unlocked configuration, the locking mechanism preventing movement of the second end within the cartridge chamber while in the locked configuration. In general, the methods of using the syringe may include the steps of expelling a liquid from the first chamber through the outlet by moving the cartridge within the first chamber, increasing pressure within the cartridge chamber by moving the second end of the cartridge within the cartridge chamber, opening the valve with the increased pressure within the cartridge chamber, and expelling a second liquid from the cartridge chamber through the valve and through the outlet by further moving the second end of the cartridge within the cartridge chamber.

The syringe devices, systems, methods, and any combination thereof described herein provide at least the following advantages. First, the syringe described herein does not rely on the fluid in the proximal chamber to expel the primary fluid (medicine) from the syringe. Therefore the syringe as described is more versatile and reliable. Second, the syringe includes a physical locking mechanism such that the intermediate fluid cannot be expelled accidentally due to increased pressure. This is an advantage, because in some prior syringes that are adapted to deliver multiple fluids but lack a physical locking mechanism, the valve is opened and the intermediate fluid (flushing liquid) is expelled simply due to increased pressure. In use, a caretaker will typically eject air from the distal chamber prior to drawing a medicine into the distal chamber. In pushing the air from the distal chamber, the caretaker could easily increase pressure in the proximal chamber and open the valve, and therefore accidentally expel the flushing liquid. A physical locking mechanism, as described herein, will therefore provide an advantage.

Additionally, the syringe described herein provides the advantage that it allows the filling oldie proximal chamber from the distal end (during manufacturing), which enables complete filling of the proximal chamber without trapping any large/non injectable air bubbles. Some prior an syringes that are adapted to deliver multiple fluids require filling procedures that include placing an intermediate sliding stopper into a conventional syringe barrel, then backfilling the proximal chamber with a liquid, such as saline, and subsequently installing the plunger assembly. By filling the proximal chamber with saline before installing the conventional syringe plunger, the prior art syringe has the disadvantage of reliance on the compressibility of the gas trapped in the proximal chamber for a successful installation of the plunger. Furthermore, the prior art syringe has the disadvantage that the distal chamber must be filled with a fluid, such as a medicine, before the saline chamber is filled as described in more detail below.

Additionally, the syringe described herein allows caregivers to follow their standard syringe filling procedures. Some alternative syringes that are adapted to deliver multiple fluids require that they be provided to a caregiver with prefilled proximal (saline) and distal (medicine) chambers. Therefore, caregivers cannot follow their standard filling procedures. For onsite usage most medicines come in multidose bottles. The most common procedure a clinician uses to fill an empty syringe with medication includes the steps of (1) fitting a syringe with a needle (metal or plastic) to penetrate the seal on a medicine bottle; (2) pulling the handle of the syringe back (proximally) to draw air into the syringe of equal or greater volume than the medicine that is to be withdrawn; (3) inserting the air filled syringe with attached needle into the medicine bottle; (4) depressing (pushing distally) the plunger to inject the air into the medicine bottle; (5) pulling the handle of the syringe back (proximally) to draw medicine from the bottle into the syringe; and (6) withdrawing the needle/syringe from the medicine bottle and removing the needle from the syringe. Prior syringes that are adapted to deliver multiple fluids cannot be used in this procedure for at least the reason that during Step 4, after injecting all the air from the distal chamber of the syringe into the medicine bottle, the plunger will collide with the internal surface of the inside of the syringe barrel. This collision causes the displaceable valved stopper to open and remain open. Once the valve is open, pulling back on the plunger would cause medicine to flow through the open valve and mix with the contents of proximal chamber. Alternatively, if the forward force were continually applied, after the valve was opened, the contents of the proximal chamber would flow through the open valve into the medicine bottle. Neither one of these scenarios is desirable. The syringe described herein, including a physical locking mechanism and separate cartridge (including an inner barrel), is ideally suited for a caregiver's standard filling procedure.

A further advantage of the syringe described herein is that it does not limit the volume of medicine that can be filled into the distal chamber. A disadvantage of some prior syringes that are adapted to deliver multiple fluids is that the volume of medicine that can be filled into the distal chamber is limited by the presence of the proximal chamber. In general the greater diameter the syringe barrel has the less exact a measurement of volume can be made by reading the fluid meniscus against gradations marked on the outside of the syringe. The specificity required is generally related to the total volume of medicine to be administered. To solve this problem clinicians use a wide range of syringe sizes depending on the amount of medication to be administered. Syringes from 1 ml to 60 ml are the most commonly used sizes. In the alternative syringes that are adapted to deliver multiple fluids the proximal chamber defined by the sliding stopper takes up space within the standard syringe barrel (the effective volume for medication is decreased by the proximal chamber by about a factor of 2) and therefore clinicians would have to use a relatively larger syringe barrel size and therefore less accurate to attempt to administer the same volume of medicine. Tire syringe described herein includes a separate cartridge that includes the proximal chamber, and therefore does not negatively impact the size of the distal chamber and its capability to hold a volume of medicine.

Figure 4:
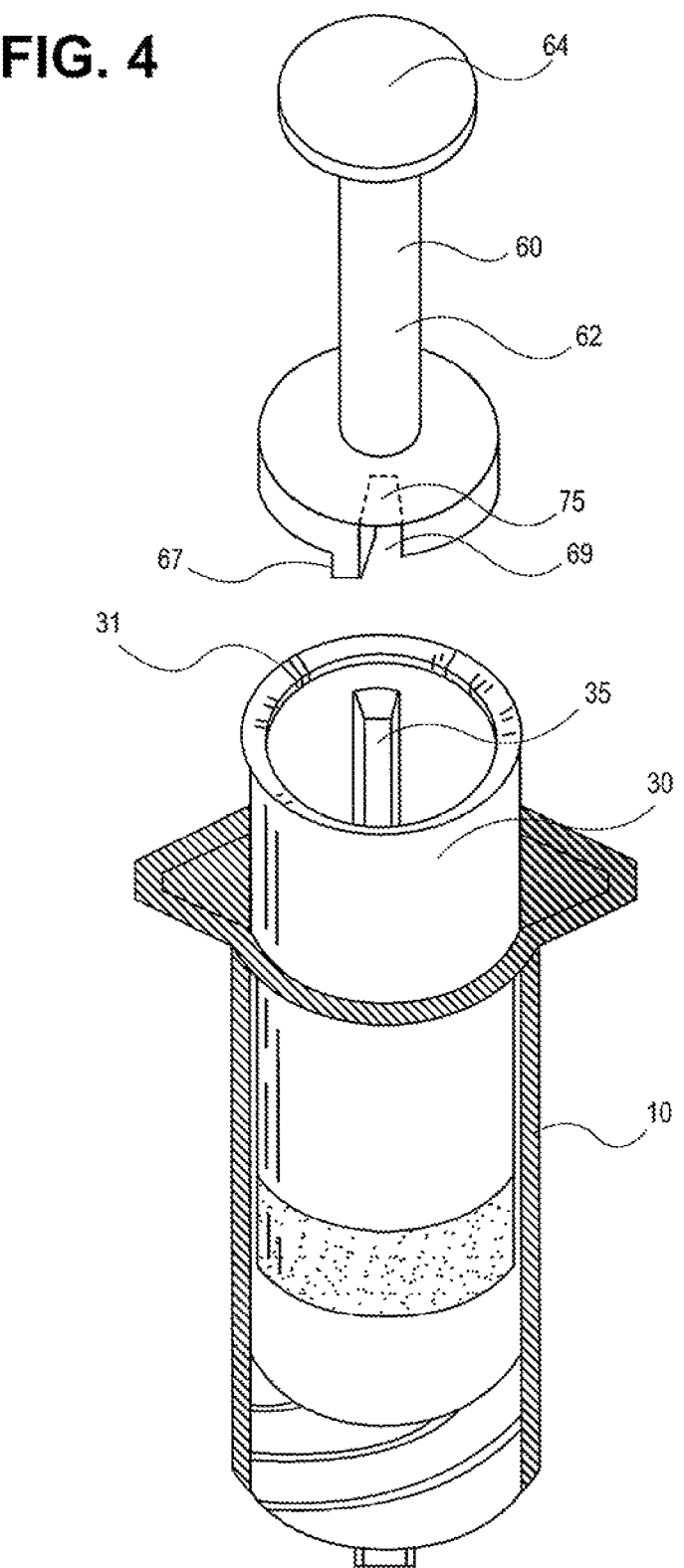
FIG. 4 is a perspective view of the embodiment depicted in FIG. 2.
Figure 5:
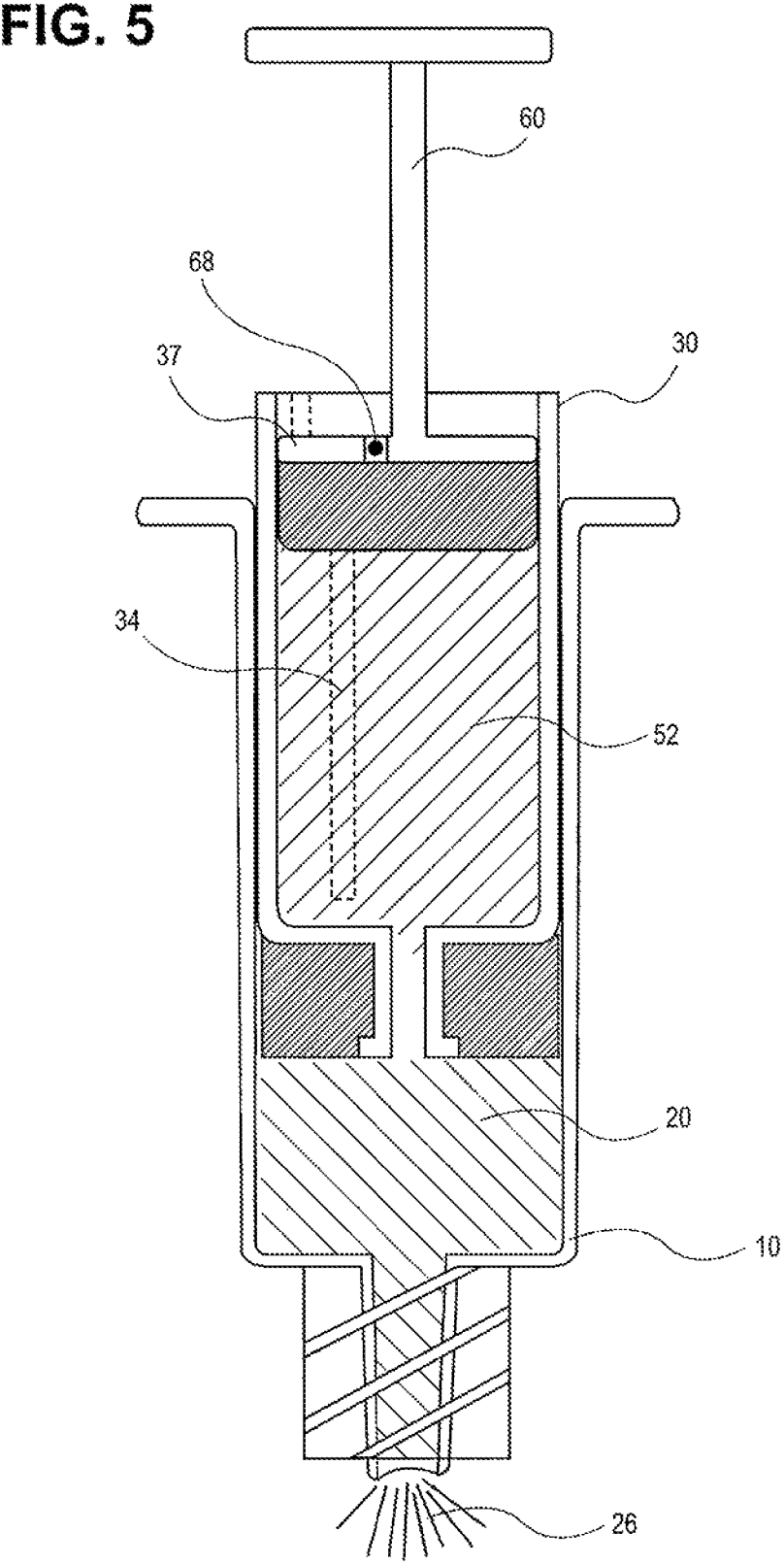
FIG. 5 is a side cross-sectional view of the embodiment depicted in FIG. 1, with the inner barrel/first piston full of a liquid such as a saline solution.

The present invention is a two-chambered syringe with three basic components: (i) an outer barrel 10 for holding a first liquid 26, (ii) an inner barrel/first piston 30 for holding a flushing liquid 52, and (iii) a second piston 60. See FIG. 5. The syringe also includes a latching mechanism for controlling the movement of the second piston 60 in the inner barrel/first piston 30. See FIGS. 3 and 4.

Figure 6:
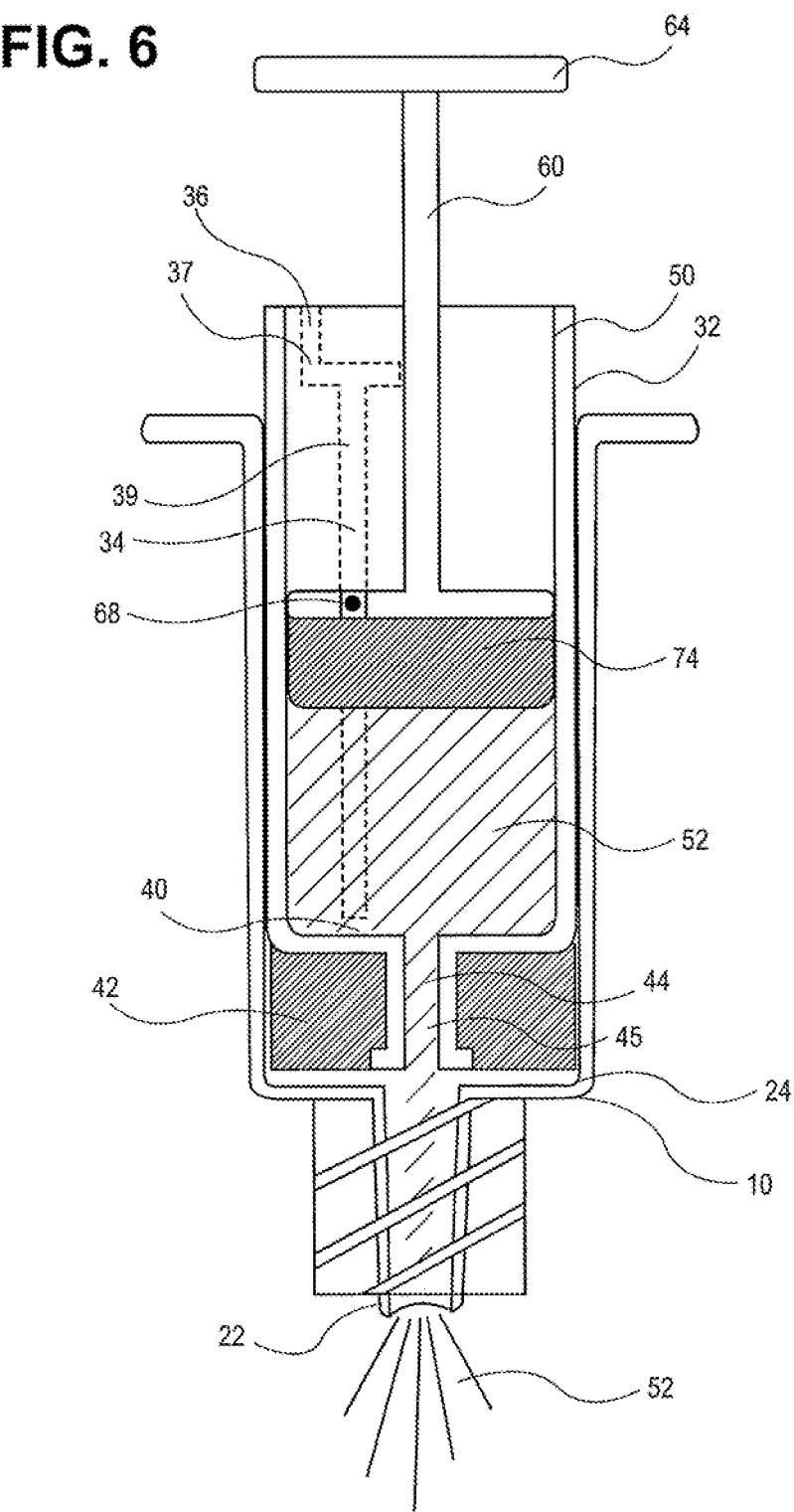
FIG. 6 is a side cross-sectional view of the embodiment depicted in FIG. 1, with the second piston partially depressed, thereby expelling some of the liquid.
Figure 9:
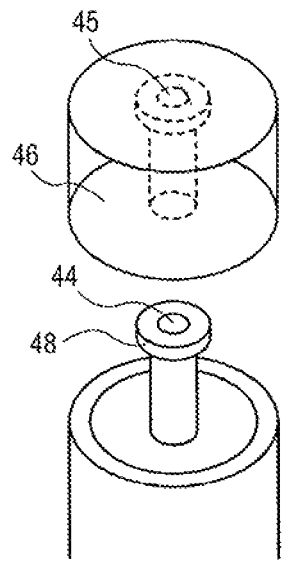
FIGS. 9-14 are perspective views of the proximal end of the second piston and sealing ring according to alternative embodiments of the present invention.
Figure 10:
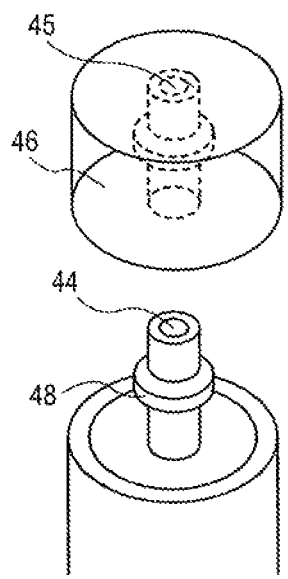
Figure 11:
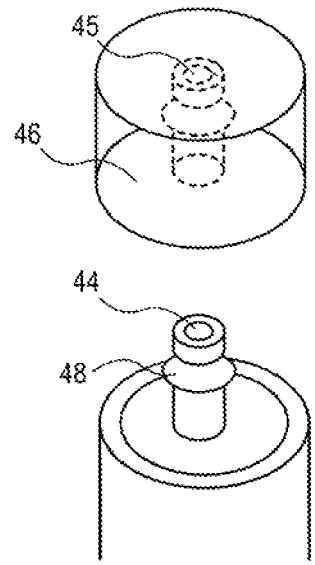
Figure 12:
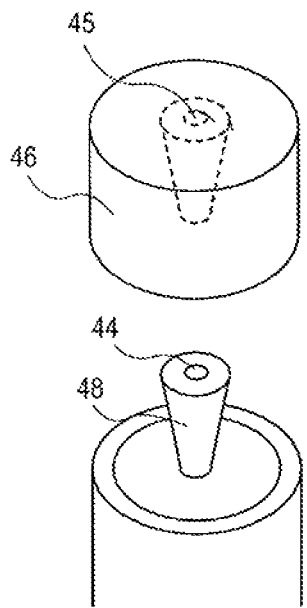
Figure 13:
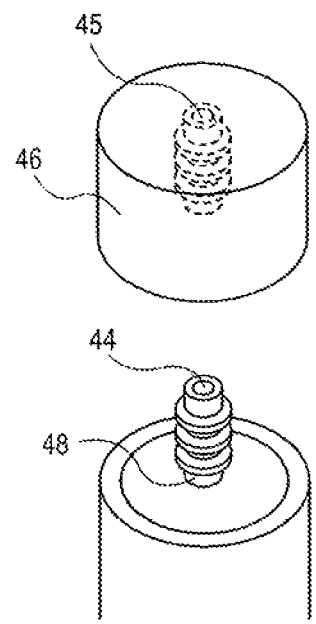
Figure 14:
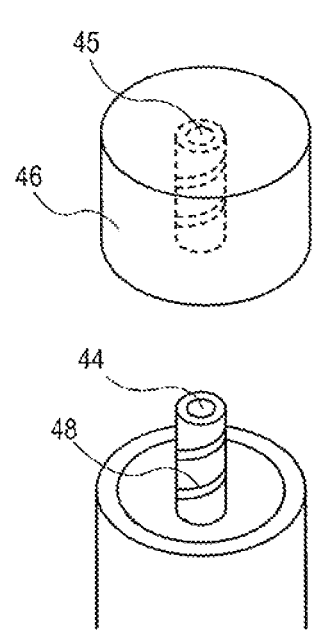
Figure 15:
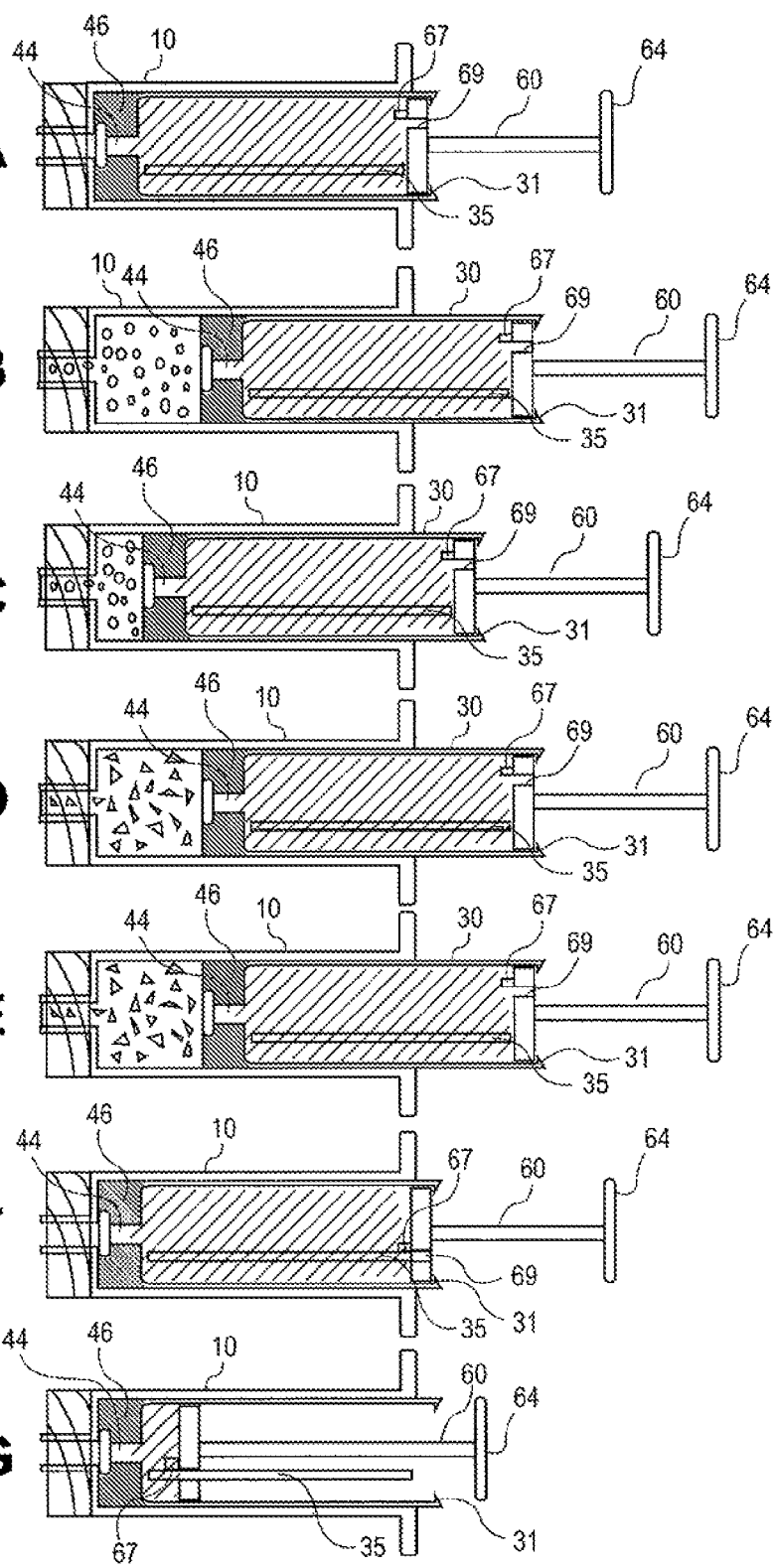
FIGS. 15(a)-(g) are side cross-sectional views of various stages of operation of the two-chambered syringe depicted in FIG. 1.
Figure 16:
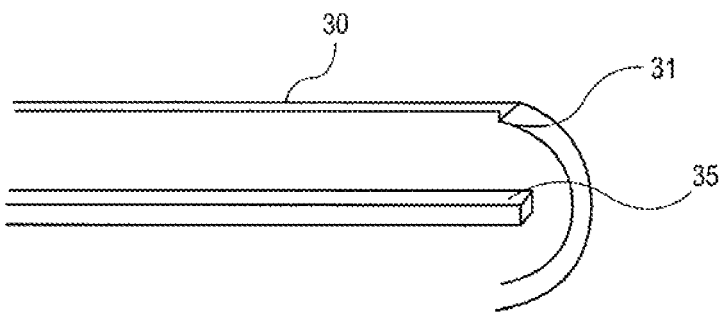
FIG. 16 is a perspective cut away view of the inner barrel/first piston showing the raised track and rear lip.

The barrels and pistons may be constructed of polypropylene or other similar inert, nonreactive semi-flexible material. Both barrels 10, 30 are generally circular cylinders. The inner barrel/first piston 30 acts as both a barrel and a piston. That is, it both holds liquid like a barrel, and may be used as a plunger to expel liquid from the outer barrel 10. See FIGS. 5 and 6.

For purposes of this patent, the proximal end of the syringe is the end typical comprising a first conduit 20, while the distal end is the end of the syringe typically comprising the second piston 60 and a gripping handle 64. See FIGS. 1 and 2.

The outer barrel 10 has an outer barrel distal open end 14 adapted for receiving the inner barrel/first piston 30. See FIG. 1. The inner barrel/first piston 30 is slidably contained in outer barrel 10 in a liquid-tight relation, similar to the piston or plunger in syringes common to the art. See FIGS. 1-6 and 15.

In one embodiment, a proximal end 16 of the outer barrel 10 may comprise an adapter 18, such as a luer connector device as disclosed in U.S. Pat. No. 4,452,473, or other locking means common in the art. See FIG. 1. The adapter 18 allows a connection between the present invention and an intravenous system. An outer barrel open proximal end 22 is at the proximal end 16 of the outer barrel 10 and may contain a first conduit 20. See FIG. 1. The distal end of first conduit 20 is in communication with the proximal end 16 of the outer barrel 10, providing a passageway for fluid from either the outer barrel 10 or the inner band/first piston 30. See FIG. 1.

The inner baud/first piston 30 has an inner barrel/first piston proximal end 40 slidably received within the outer barrel open distal end 14. See FIG. 1. It also includes a hollow projection 42 that extends proximally out of the inner barrel/first piston 30. See FIGS. 1, 9-14. The hollow projection 42 defines a second conduit 44 through which liquid flows from the inner barrel/first piston 30 to the outer barrel 10. See FIGS. 1 and 6-8. The hollow projection 42 has a flared tip 48 that secures a first sealing ring 46, as shown in FIGS. 7 and 8. The flared tip 48 may take many different forms, as shown in FIGS. 9-14.

The first sealing ring 46 comprises a sealing ring conduit 45 through which extends the hollow projection 42. See FIGS. 7-14. The first sealing ring 46 is substantially the same diameter as both the inner barrel/first piston outer wall 32 and the outer barrel inner wall 24, creating, a liquid tight seal between the inner barrel/first piston 30 and the outer barrel 10. See FIG. 6. Thus, the only fluid connection between the inner barrel/first piston 30 and the outer barrel 10 is through the second conduit 44 and the sealing ring conduit 45. The sealing ring 46 may be constructed of an elastic, material such as natural or synthetic rubber.

The flushing liquid 52 is inside the inner barrel/first piston 30. See FIGS. 5, 5-6. The flushing liquid 52 may be a saline solution, or any other suitable solution, such as heparin, when anticoagulation is desired, or antibiotics, when a line infection is being treated.

The flushing liquid 52 occupies substantially all of the space defined by the inner barrel/first piston inner wall 50, and initially extends partially through the second conduit 44 defined by the hollow projection 42. See FIGS. 5 and 15. Because the flushing liquid 52 only extends partially through the second conduit 44, the flushing liquid 52 remains isolated from any liquid later drawn into the outer barrel 10.

Figure 17A:
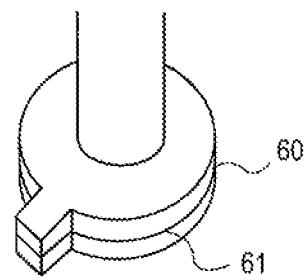
FIGS. 17(a) and (b) are perspective views of a portion of the inner barrel of a two-chambered syringe according to an embodiment of the present invention.
Figure 17B:
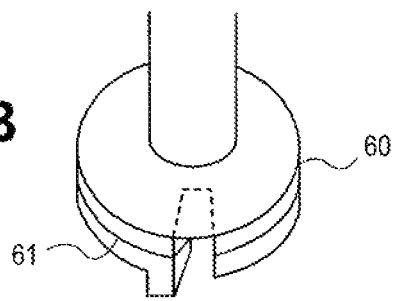

The second piston 60 is slidably placed within the inner barrel/first piston 30. See FIGS. 3-5 and 15. The second piston 60 comprises a second piston proximal end 66 further comprising a solid projection 70 that fits through an aperture 76 in a second sealing ring 72, thereby attaching the second piston 60 to the second sealing ring 72. See FIGS. 1, 3. The second sealing, ring 72 is of substantially equal diameter to the inner barrel/first piston inner wall 50, and is created from an elastic rubber-like material that provides a liquid-tight seal for the inner barrel/first piston 30. See FIG. 3. Alternatively, this liquid-tight seal may be created by a similar rubber-like sealing material 61 placed around the periphery of the proximal end of the second piston 60. See FIG. 17. The second piston 60 moves in and out of the lumen of inner barrel/first piston 30, thereby dispensing liquid from or drawing liquid into the inner barrel/first piston 30. See FIG. 3.

Extending distally from second piston proximal end 66 is a piston rod 62. See FIGS. 3 and 4. A gripping handle 64 is placed at the most distal end of the second piston 60.

The two-chambered syringe further comprises a latching mechanism that can alternate between an unlocked configuration and a locked configuration. See generally FIGS. 3-4 and 7-8. In the locked configuration, the second piston 60 is longitudinally locked relative to the inner barrel/first piston 30. See FIG. 15(b). In this configuration, the second piston 60 will not move longitudinally relative to the inner barrel/ first piston 30. See FIGS. 5 and 15(a)-15(e). However, a longitudinal force applied to the second piston 60 will be transferred proximally and the inner barrel/first piston 30 will move relative to the outer barrel 10.

In the unlocked configuration, the second piston 60 is free to move longitudinally relative to the inner barrel/first piston 30. See FIGS. 6 and 15(f)-15(g). Thus, the contents of the inner barrel/first piston 30 are ejected through the second conduit 44 when the second piston 60 is depressed. When the second piston 60 is retracted, the inner barrel/first piston 30 will provide sufficient suction to draw in the contents of the outer barrel 10 through the second conduit 44.

In one embodiment, the latching mechanism comprises a projection 68, extending outward radially from near the second piston proximal end 66. See FIGS. 1 and 3. In this embodiment, the projection is constructed of a polypropylene or other similar inert, nonreactive semi-flexible material the same as or similar to that comprising the barrels and pistons of the syringe. While the radial width of the projection 68 shown in FIGS. 1 and 3 is small relative to the distance around piston rod 62, the same principle preventing movement of the piston rod 62 would apply regardless of the radial width or shape of projection 68. See FIG. 3.

This projection fits snugly into a groove 34 cut into the inner barrel/first piston inner wall 50, thereby allowing the second piston 60 to only move according a path of movement defined by groove 34. See FIGS. 3 and 6.

The groove 34 includes a longitudinal portion 39 extending longitudinally along the inner barrel/first piston inner wall 50, ending at the inner barrel/first piston proximal end 40. See FIG. 6. Near the distal end of the inner barrel/first piston 30, the longitudinal portion 39 makes a substantially right angle and continues circumferentially around the inner barrel/first piston inner wall 50 as a radial portion 37. See FIGS. 3, 6, and 8. In one embodiment, the radial portion 37 of the groove 34 extends less than one half of one revolution of the perimeter around the inner barrel/first piston inner wall 50. See FIGS. 7 and 8.

In one embodiment, the groove 34 continues to substantially the distal end of inner barrel/first piston 30, outlining a track ultimately leading to a projection entry point 36. See FIGS. 3, 6, 7. The projection entry paint 36 serves as art entrance to the groove 34 for the projection 68, simplifying the assembly process for the syringe, and reducing the cost of construction. In the alternate embodiment, shown in FIG. 8, the second piston 60 with protrusion 68 would be installed into the inner barrel by applying sufficient pressure to temporarily flex the plastic allowing a press-fit construction. See FIGS. 3 and 8.

When the second piston 60 is in the fully extended position, the projection 68 will lie in the radial portion 37 of the groove 34. See FIG. 5. From this position, the second piston 60 may be axially rotated, and the projection 68 will slide along the radial portion 37 of the groove 34. Additionally, the second piston 60 and the inner barrel/first piston 30 are longitudinally locked together, and in this fixed position the two components function collectively as one piston relative to the outer barrel 10. See FIGS. 5 and 15(a)-15(e). The syringe may then be used in the same manner as a conventional one-chambered syringe.

In yet another embodiment, instead of comprising a track defined by an indented groove on the inner barrel/first piston 30, the syringe comprises a track defined by a raised track 35 outlining the same path previously defined by the groove 34. See FIGS. 2-4, and 16. Correspondingly, the second piston 60 comprises an indentation 69 instead of the projection 68. See FIGS. 2-4. In this configuration raised track 35 fits snugly into indentation 69, thus defining a track for the second piston 60 to follow when in the unlocked position. See FIGS. 2 and 4. In this embodiment, the track need not extend longitudinally the entire length of the inner barrel to accomplish the locking feature.

To ensure the saline does not leak backwards out of the flush chamber, the second piston 60 may additionally comprise breakaway guard 75, which provides a cover over the indentation 69. The breakaway guard 75 may be a layer of plastic that is capable of being punctured by raised track 35 when the operator applies sufficient force. The operator of the syringe will feel the resistance and subsequent release as the breakaway guard is punctured. See FIGS. 2, 4, and 16. The need for this guard may be circumvented by making a rear lip 31 large enough to prevent backward flow of the flush solution. The lip 31 of the inner barrel enables a unidirectional press fit construction (due to the sloped angle of the lip 31) in which the second plunger may be easily slid into the inner barrel, but cannot be easily removed. Thus, the second piston 60 is effectively trapped between the raised track 35 and the lip 31 thus preventing the second piston from moving longitudinally with respect to the inner barrel/first piston when the second piston is in the locked configuration. See FIGS. 15(a)-15(f).

Other latching mechanisms may be used, and for purposes of this patent, "latching mechanism" refers generically to any structure that can lock and unlock the inner barrel/first piston 30 relative to the second piston 60. See FIG. 1.

One advantage of applicant's device is that the syringe may function as a traditional syringe, independent of the internal flush chamber in the inner barrel/first piston 30. See FIGS. 15(b)-15(e). Additionally, this syringe may be used to dispense a flush solution without filling the outer chamber with a second liquid or gas.

In operation, the syringe will typically first be in the locked position so medicine withdrawn from a bottle fills the outer chamber 10. See FIG. 15(a)-(d). When medication is administered directly to a vein, a clinician using a traditional syringe will often confirm that a vein has been pierced by drawing a small amount of blood into the syringe, prior to injection of the medication. This device allows for this normal operation to be performed when the device is in the locked configuration. See FIGS. 15(b)-15(c).

Because the flushing liquid 52 does not extend through the second conduit 44, it will not mix with fluid drawn into the outer chamber 10. In a separate embodiment, flushing liquid 52 extends only partially through the second conduit 44, but not enough to mix with fluid drawn into outer chamber 10. The two fluids will not come in contact with each other due to basic fluid mechanics. That is, surface tension of the fluid drawn into the outer chamber 10 prevents it from entering the second conduit 44. The flushing liquid 52 does not move through the second conduit because as it completely fills the inner barrel/first piston 30, the negative pressure created inside the outer barrel 10 when fluid is drawn in, is not great enough to displace the flushing liquid 52 from the inner barrel/first piston 30.

Next, while the syringe is still in the locked configuration, the contents of the outer barrel 10 may be delivered to a patient by depressing the second piston 60. See FIGS. 15(e)-15(f). After injecting the medication, the operator may axially rotate the second piston 60 until the longitudinal portion 39 of either the groove 34 or the track 35 defines the path of movement. See FIGS. 6 and 15(f)-15(g). In the embodiments shown in FIG. 2 and FIG. 8 the clinician may confirm this alignment upon feeling that the axial rotation is halted by forward projection 67. In the embodiments shown in FIG. 1 and FIG. 3, a clinician may confirm this alignment by rotating the second piston 60 until an indicating mark on second piston 60 is longitudinally in line with a mark on the inner barrel/first piston 30 or the outer barrel 10. From this position, the second piston 60 may be longitudinally moved down the length of the inner barrel/first piston 30, thereby emptying the contents of the inner barrel/first piston 30 into the outer barrel 10 and then into the catheter. See FIGS. 6 and 15(f)-15(g).

In the embodiment shown in FIG. 2, after the outer barrel is dispensed the second plunger may be rotated axially until the forward protrusion 67 meets the raised track 35, impeding further rotation. From this position, proper alignment of the track and indentation is assured because the forward protrusion 67 is adjacent to the indentation 69. Next, the operator would depress the second piston 60 a second time, emptying the contents of the inner barrel through second conduit 44. See FIGS. 6 and 15(f)-15(g). Preferably, at this point in the process, the medication from the outer barrel 10 is already expelled into the intravenous system, and thus the contents of the inner barrel/first piston 30 may be used to flush any remaining medication into the patient.

Figure 18A:
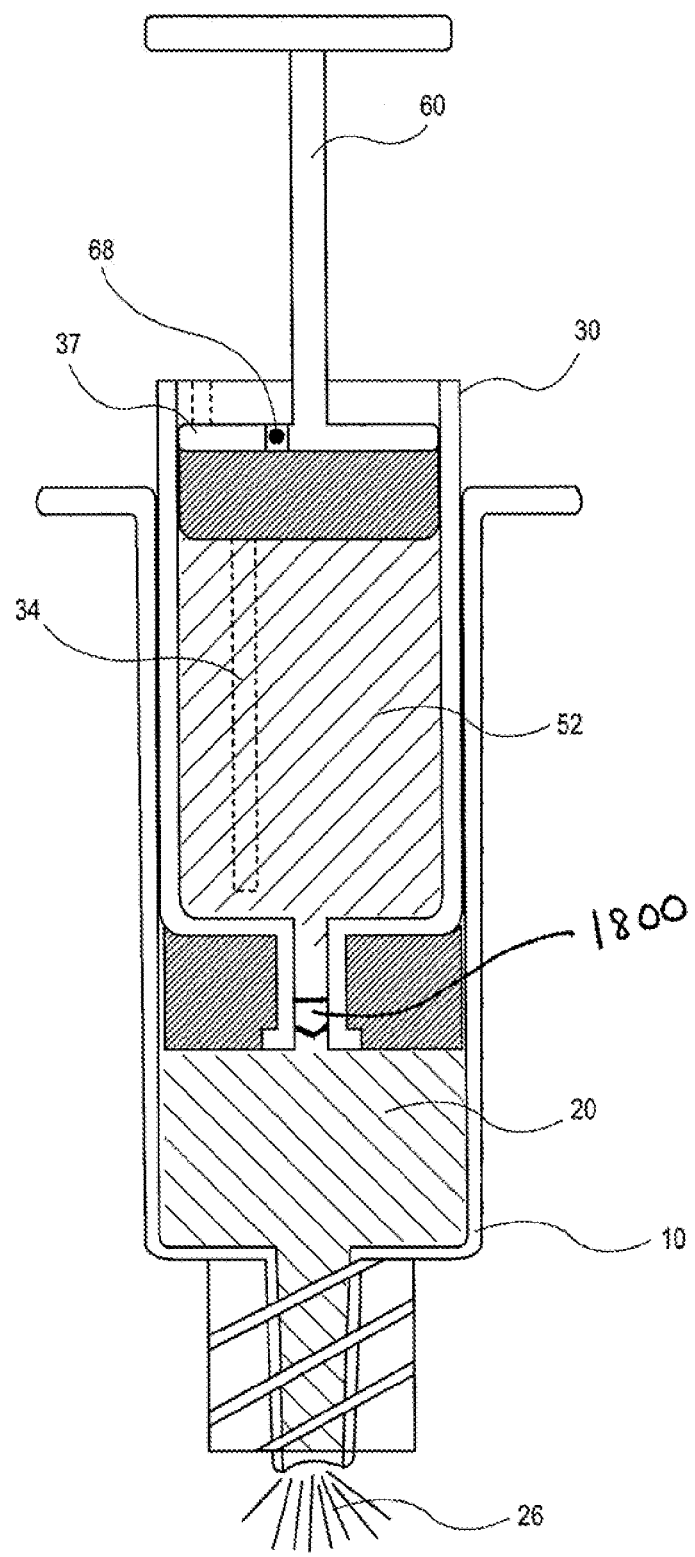
FIGS. 18A-18D illustrate an embodiment of the syringe having a valve.

As shown in FIG. 18A, and as described above, a variation of the present invention can include an outer barrel 10 and a cartridge that is movable within the outer barrel 10. The cartridge can include an inner barrel/first piston 30 having a first end which defines a channel or conduit 44 that is in fluid communication with the outer barrel 10 and the inner barrel.

Figure 18D:
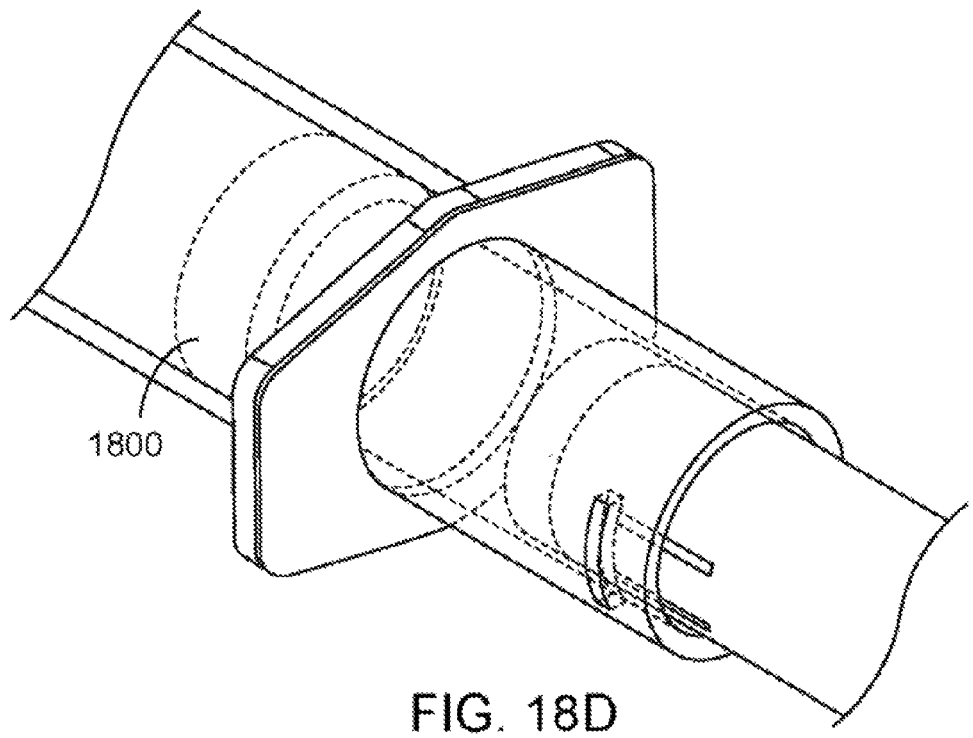
Figure 18B:
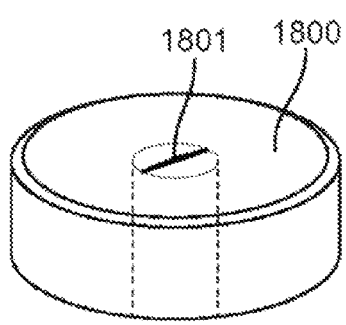
Figure 18C:
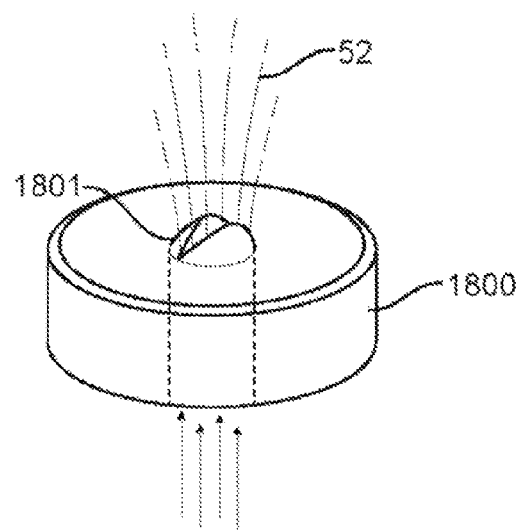

This variation of the cartridge also includes a valve 1800 in fluid communication with the cartridge chamber (inner barrel/first piston 30) and the distal chamber (outer barrel 10). The valve has a closed configuration, as shown in FIG. 18B, and an open configuration, as shown in FIG. 18C. The valve allows movement of a liquid 52 out of the cartridge chamber while in a open configuration. The cartridge also includes a second end that is movable within the inner barrel. In some embodiments, the second end comprises second piston 60. The cartridge may further include a locking mechanism (having groove 34 as shown in FIG. 18D). The locking mechanism prevents movement of the second end within the inner barrel while in the locked configuration. The outer barrel defines a distal chamber and the inner barrel of the cartridge defines a proximal chamber. The distal chamber will typically hold a medicine, while the proximal chamber will typically hold a flushing liquid 52 such as saline.

The cartridge is nearly rigid; the volume contained within the cartridge of the syringe is constant if the second end (second piston 60) is fixed in position by the locking mechanism. When this is the case, as long as the fluid volume and/or pressure in the inner barrel 30 is unchanged, the valve 1800 will remain in the closed configuration, preventing the movement of the liquid 52 out of the cartridge. When the locking mechanism is unlocked and the second end is depressed, the pressure in the cartridge is increased by the forward flow of liquid 52 causing the valve to open and the liquid to be expelled through the valve.

As shown in FIGS. 18B and 18C, the valve is a one-way valve including flaps 1801 that are biased toward the closed configuration. As shown in FIG. 18B, in the closed configuration, the flaps are touching one another. As shown in FIG. 18C, the flaps bend or flex away from one another such that there is an opening between them in response to an increase in pressure on the surfaces of the flaps facing the proximal chamber. In some embodiments, the valve is a duckbill valve. Duckbill valves are typically one-piece, elastomeric components that act as backflow prevention devices or check valves. They have elastomeric "lips" or flaps in the shape of a duckbill which prevent backflow and allow forward flow. Alternatively, the valve 1800 may be any other suitable valve such as an umbrella valve, cross slit valve, or any other suitable type of one-way valve.

Figure 19:
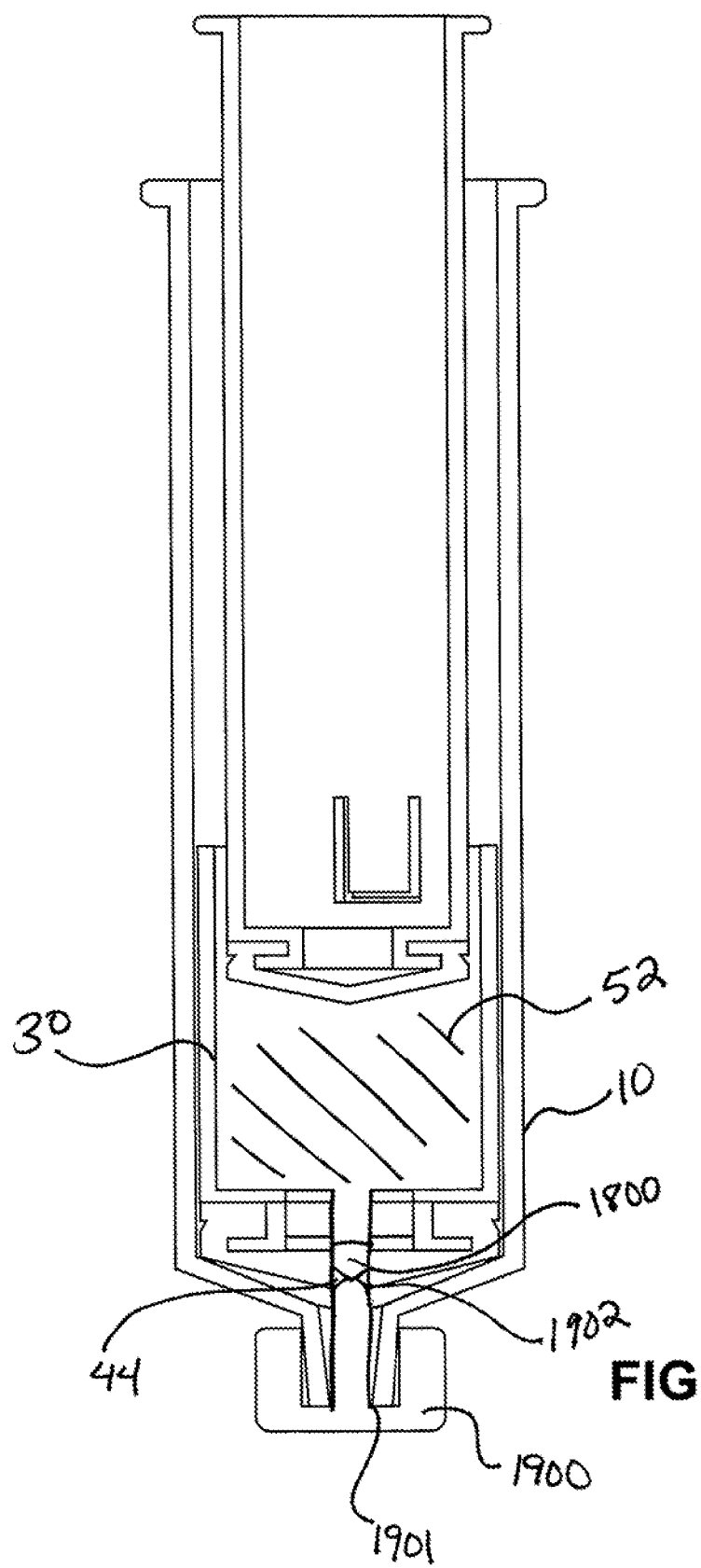
FIG. 19 is a side cross-sectional view of an embodiment of a syringe including an end cap.

In some embodiments, as shown in FIG. 19, the syringe further includes a removable end cap 1900 coupled to the outlet 1901 of the outer barrel 10 and to the channel or conduit 44 of the cartridge. As shown, the end cap includes an end surface 1902 within the conduit 44. In some variations, the end surface 1902 may be adjacent to valve 1800 and may aid in preventing the opening of the valve during storage and/or transport of the syringe. In some embodiments, the syringe is designed to be filled with saline by the manufacturer, capped with an end cap 1900 and shipped to the customer. The customer will then remove the cap, and fill the distal chamber of the outer barrel 10 with medicine as desired.

As described above, in some embodiments, the syringe is designed to be filled with a flushing liquid, such as saline, by the manufacturer of the syringe. In general, as shown in FIGS. 20A and 20B or 21A and 21B, a method of filling a syringe cartridge includes the steps of injecting a liquid 52 into the inner barrel 30, through conduit 44, and through the valve (not shown). The inner barrel chamber may be filled up to the proximal end of the conduit 44 or beyond.

As shown, the liquid 52 may be injected into the cartridge chamber via a needle or nozzle 2002 positioned within the outlet of the outer barrel 10 and the conduit 44 of the cartridge. The needle or nozzle may be inserted within the flaps or "lips" of the valve (not shown). The cartridge may be filled such that the chamber includes about 1 to 10 ml of liquid disposed within inner barrel 30. Alternatively, the cartridge comprises about 2 to 3 ml of liquid disposed within the cartridge chamber. Ideally the cartridge is filled with the smallest volume of fluid, such as saline, that can still effectively flush an intravenous catheter line, for example. In one particular embodiment, the cartridge is prefilled with 25 ml of saline. In some embodiments, the syringe may be offered in a complete line of syringes of different volumes. For example, the range of syringe sizes may include syringes that are capable of holding 1, 3, 6, 12, 15, 30, and/or 60 ml of an injectable liquid such as medicine in the distal chamber. Each syringe size may have a common flush, size in the proximal chamber, for example 2.5 ml. Alternatively, each syringe size may include a cartridge with a different flush size.

Figure 20A:
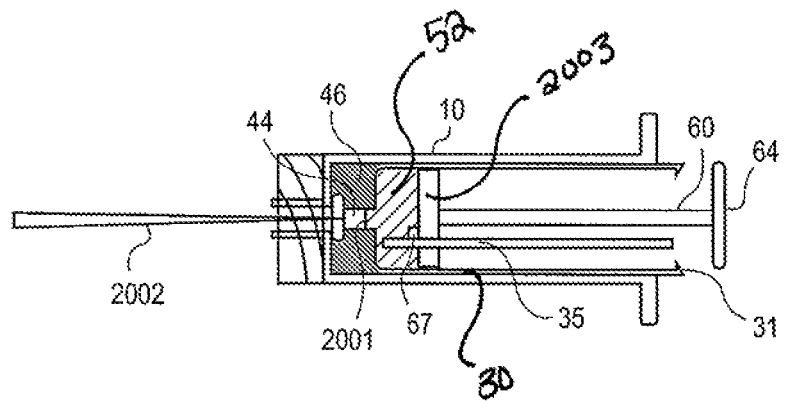
FIGS. 20A-21B illustrate multiple embodiments of a method of filling a syringe.
Figure 20B:
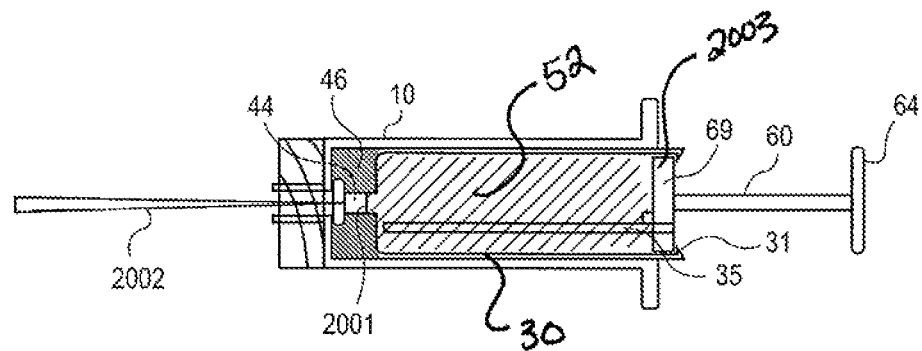

As shown in FIGS. 20A and 20B, the injecting step comprises injecting a liquid into the inner barrel 30 through the outlet of the outer barrel of the syringe and the conduit 44 of the cartridge. Again, the needle or nozzle may be inserted within the flaps or "lips" of the valve (not shown). As shown, the cartridge is positioned at the distal end of the outer barrel 10. As shown in FIG. 20A, the second end 2003 of the cartridge is positioned at the distal end of the inner barrel 30. As the liquid 52 is injected into the inner barrel 30 of the cartridge, the volume of liquid 52 increases. The liquid pushes the second end 2003 of the cartridge in the proximal direction such that the proximal chamber of the inner barrel 30 expands as it is filled with liquid 52, as shown in FIG. 20B. In some embodiments, the inner barrel 30 will be filled until the locking mechanism is engaged and the second end 2003 is locked with respect to the cartridge.

Figure 21A:
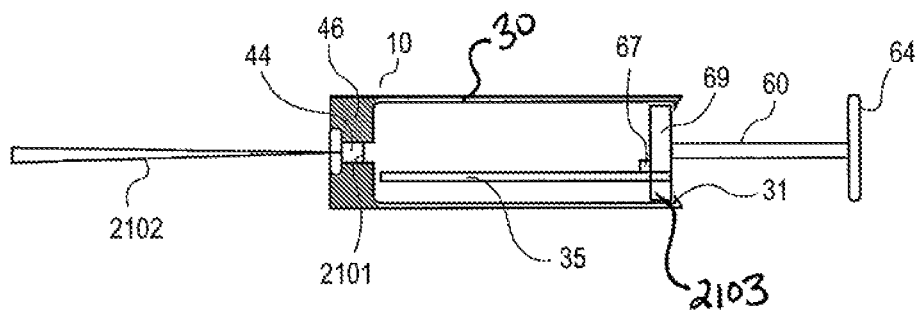
Figure 21B:
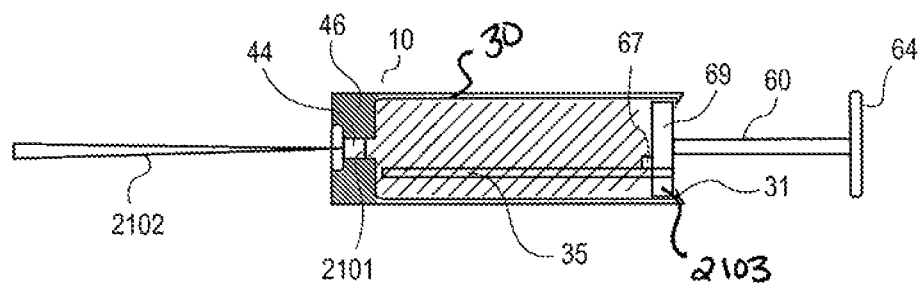

As shown in FIGS. 21A and 21B, in some embodiments, the cartridge (including inner barrel 30, first end 46 having conduit 44 and valve (not shown), and second end 2103) is filled independently from the outer barrel not shown). The liquid 52 may be injected into the cartridge chamber via a needle or nozzle 2102 positioned within the conduit 44 of the cartridge and within the valve. Once filled, the cartridge may then be placed within the outer barrel, such that the cartridge is movable within the outer barrel. As shown in FIG. 21A, the second end 2103 of the cartridge is positioned at the proximal end of the inner barrel 30. As the liquid 52 is injected into the inner barrel 30 of the cartridge, the liquid 52 fills the volume of the chamber within the inner barrel, as shown in FIG. 21B. In this embodiment, the needle does not completely occlude the valve and conduit 44 such that air is allowed to escape as the cartridge is filled with saline. Alternatively, the liquid 52 can move the second end 2103 of the cartridge proximally to expand the cartridge chamber as the inner barrel is filled, as described above.

In an alternative embodiment, the syringe cartridge may be filled through the proximal end of the inner barrel, prior to inserting the second end of the cartridge into the inner barrel. In this embodiment, the first end of the cartridge may be temporarily occluded while the cartridge is filled through the open proximal end of the inner barrel. Once filled the second end of the cartridge may be positioned within the filled inner barrel, and in some embodiments locked in place with respect to the inner barrel by the locking mechanism. Once the chamber of the cartridge is closed off by the second end of the cartridge, the occlusion from the first end of the cartridge can be removed such that air trapped in the cartridge during the filling and positioning of the second end may escape.

Once a user receives a syringe, in some cases having a prefilled cartridge, filling the medicine chamber (outer barrel 10) follows the standard operation for filling a syringe, which includes the steps of (1) fitting a syringe with a needle (metal or plastic) to penetrate the seal on a medicine bottle; (2) pulling the handle of the syringe back (proximally) to draw air into the syringe of equal or greater volume than the medicine that is to be withdrawn; (3) inserting the air filled syringe with attached needle into the medicine bottle; (4) depressing (pushing distally) the plunger to inject the air into the medicine bottle; (5) pulling the handle of the syringe back (proximally) to draw medicine from the bottle into the syringe; and (6) withdrawing the needle/syringe from the medicine bottle and removing the needle from the syringe.

The syringe may then be connected to the patient or patient line at a luer port for injection of the medicine. The handle is depressed to inject the medicine, then the cartridge is unlocked and the handle is depressed further to open the valve and inject the saline. The syringe is removed and discarded.

In general, a method of using a syringe includes the steps of drawing a second liquid (such as medicine) into the outer barrel through the distal outlet by moving the cartridge proximally within the outer barrel and creating a second liquid-air interface within the conduit. In some embodiments, the method further includes the steps, or any combination thereof, of (a) expelling the second liquid (such as medicine) from the outer barrel through the distal outlet by moving the cartridge distally within the outer barrel, (b) releasing a locking mechanism from a locked configuration to an unlocked configuration to allow movement of a second end within the inner barrel, (c) increasing pressure within the cartridge chamber by moving the second end of the cartridge within the cartridge chamber, (d) opening the valve with the increased pressure within the cartridge chamber, and (d) expelling the first liquid (such as saline) from the inner barrel of the cartridge through the valve and the distal outlet by moving the second end of the cartridge distally within the inner barrel.

Figure 22A:
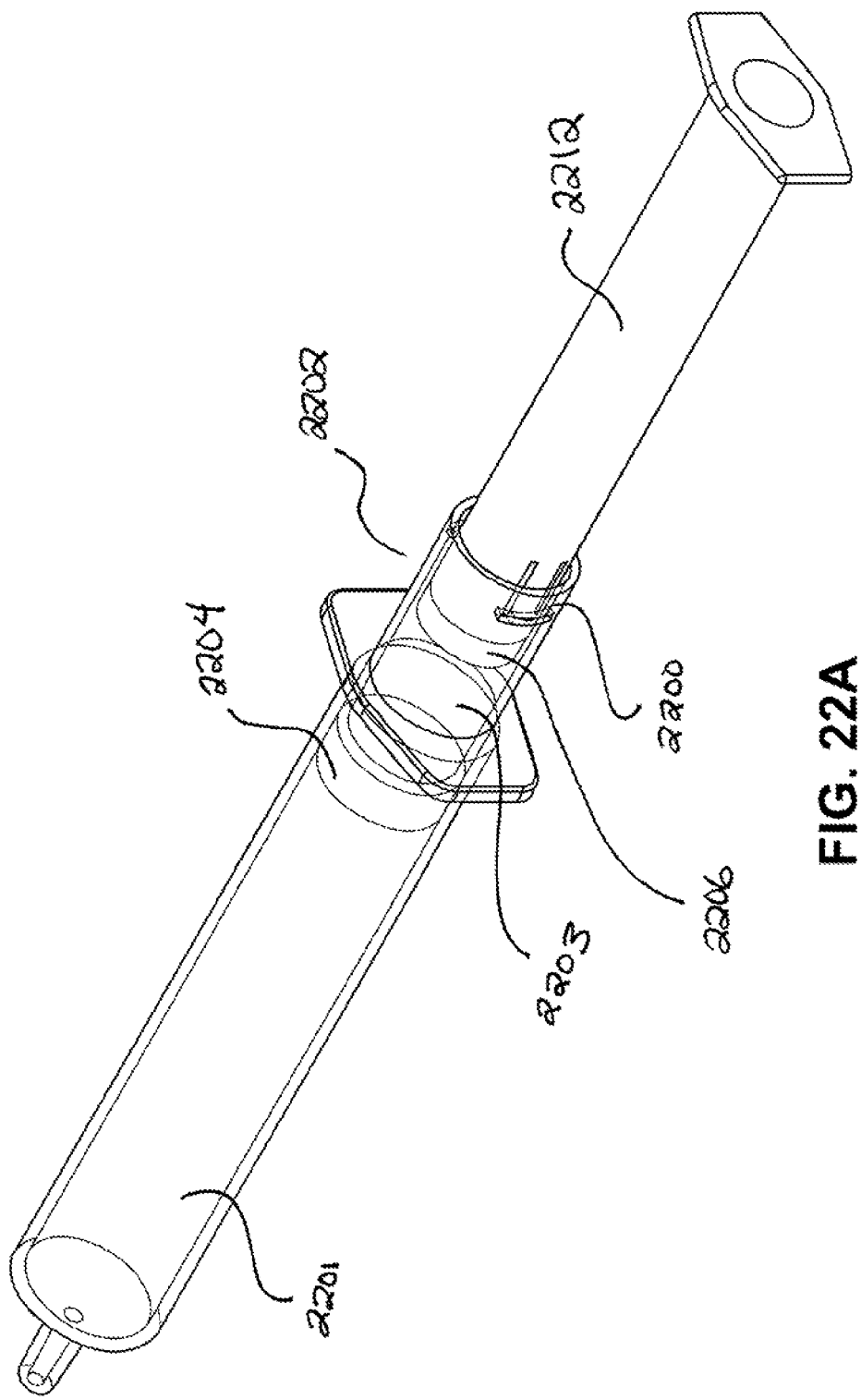

In some embodiments, as shown in FIGS. 22A and 22B, a syringe having a locking mechanism 2200 may include a first chamber 2201 and a cartridge 2202 movable within the first chamber 2201. The cartridge, as shown in FIG. 22B includes a cartridge chamber 2203, a first end 2204 that defines a channel 2205 in fluid communication with the cartridge chamber 2203 and the first chamber 2201 (of the syringe in FIG. 22A), a second end 2206, movable within the cartridge chamber, and a locking mechanism 2200 having a locked configuration and an unlocked configuration. The locking mechanism prevents movement of the second end within the cartridge chamber while in the Locked configuration, thereby preventing an increase of pressure within the cartridge chamber and preventing the opening of the valve within the channel 2205. As shown in FIG. 22B, the locking mechanism includes a flexible arm 2207 having a first end 2208 and a second free end 2209, a tab 2210 coupled to the second free end, and a groove 2211 configured to receive the tab. In some embodiments, the flexible arm is coupled to the second end 2206 of the cartridge while the groove is defined by the inner barrel or cartridge chamber of the cartridge. As shown in FIG. 22A, the syringe may further include a handle 2212 coupled to the second end of the cartridge. In some embodiments, the flexible arm of the locking mechanism may be coupled to the handle as shown. Alternatively, the tab type locking mechanism 2200 can comprise a resistance type lock. For example, the chamber 2201 and cartridge 2202 shall remain locked until the cartridge 2212 bottoms out against the chamber 2201 upon which time increased pressure at the handle causes detachment of the resistance lock 2200.

The geometry of the groove is such that it receives the tab and holds the tab in place, preventing movement of the second end with respect to the cartridge chamber. The geometry of the groove is such that the tab can be moved in and out of the groove in the circumferential direction, i.e. by rotating the second end of the cartridge with respect to the cartridge chamber. The tab cannot be moved in and out of the groove in the axial direction (i.e, proximally or distally). Once the tab is rotated out of the groove, however, the locking mechanism is in the unlocked configuration, and the tab may be moved proximally or distally with respect to the groove, and therefore the second end may be moved proximally or distally with respect to the cartridge chamber.

The flexible arm is configured such that it has an equilibrium configuration, and a bent configuration. In the equilibrium configuration, the tab extends beyond the outer surface of the second end 2206 of the cartridge and/or the handle 2212. In the bent configuration, the second end 2209 of the flexible arm is bent inward, such that the tab is within or flush with the outer surface of the second end 2206 of the cartridge and/or the handle 2212. When the flexible arm is in the bent configuration, the second end of the cartridge can move with respect to the cartridge chamber. When the flexible arm is in the equilibrium configuration the tab extends beyond the outer surface of the second end 2206. It is in the equilibrium configuration that the tab will be received by the groove and that the locking mechanism is in the locked configuration. The flexible arm is biased toward the equilibrium configuration such that once the tab reaches a groove within the cartridge, the tab will spring into the groove, thereby locking the locking mechanism. To release the tab from the groove, the tab is rotated out of the groove.

As shown in FIG. 23, the tab includes a ramped surface 2300. As the second end of the cartridge 2306 is rotated counter-clockwise (toward the top of the Figure), for example, the ramped surface interacts with the edge of the groove 2311 such that the groove pushes the tab down along the ramped surface 2300 such that the flexible arm transitions from the equilibrium configuration to the bent configuration. Once the second end 2306 is rotated sufficiently such that the tab is released from the groove, the locking mechanism is unlocked, and the second end 2306 may be moved proximally or distally with respect to the cartridge chamber 2303. In some embodiments, as shown in FIGS. 22A and 22B, the tab is substantially semi-circular shaped such that it includes two ramped surfaces. Therefore, the tab as shown in FIGS. 22A and 22B may be rotated in both the clockwise direction or in the counter-clockwise direction to release the locking mechanism. As shown in FIG. 23 the tab includes a single ramped surface 2300 and is therefore substantially triangular shaped. The tab may include any suitable number of ramped surfaces and have any suitable geometry.

Figure 24:
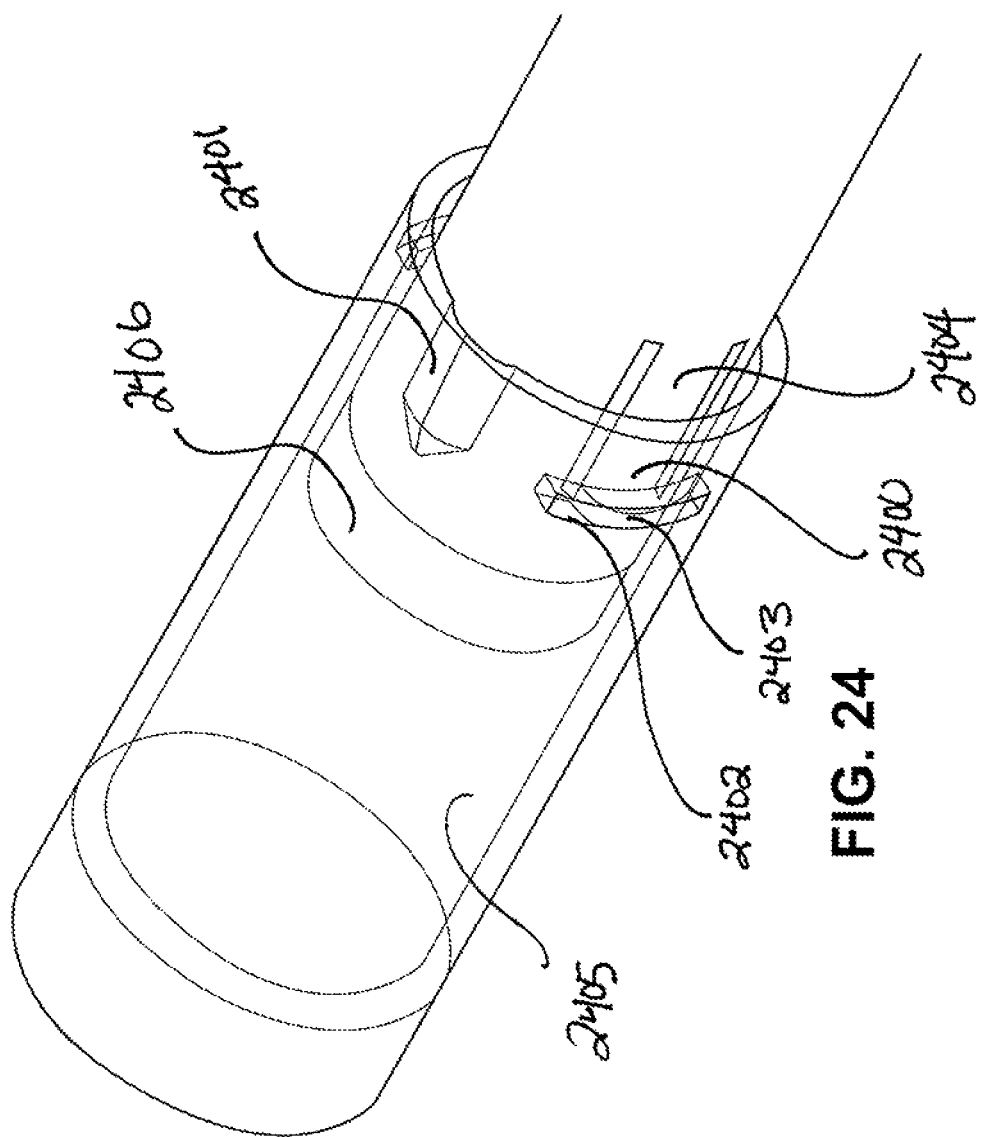
FIGS. 24-26 are perspective views of an embodiment of a syringe including a locking mechanism and additional grooves.

In some embodiments, as shown in FIG. 24, the syringe further includes an additional groove 2401 adjacent to the locking mechanism 2400. The adjacent groove is configured to receive the tab 2403 once it is rotated out of groove 2402 and when the locking mechanism is in the unlocked configuration. When the tab springs from the bent configuration back into the equilibrium configuration as the tab is received by the adjacent groove, this will signify that the locking mechanism is unlocked and that the second end 2406 of the cartridge can be moved with respect to the inner barrel. Furthermore, when the tab is received by the adjacent groove, the adjacent groove will stop or impede the rotation of the second end with respect to the inner barrel, once again signaling that the release of the locking mechanism is complete. In some embodiments, the locking mechanism may include two grooves 2403 and two flexible arms 2404 on opposite sides of the cartridge from one another. In this embodiment, the cartridge may include two adjacent grooves 2401 on opposite side from one another and about 90 degrees from the grooves 2403. The syringe may alternatively include any suitable number of locking mechanisms and adjacent grooves. The adjacent grooves are located on the inner surface of the cartridge chamber 2405. The adjacent grooves may include a tapered depth such that the adjacent groove permits movement (in the distal direction) of the second end 2406 with respect to the chamber of the cartridge 2405. The tapered depth may function to slowly transition the flexible arm from the equilibrium configuration to the bent configuration as the second end is moved distally with respect to the chamber.

Figure 25:
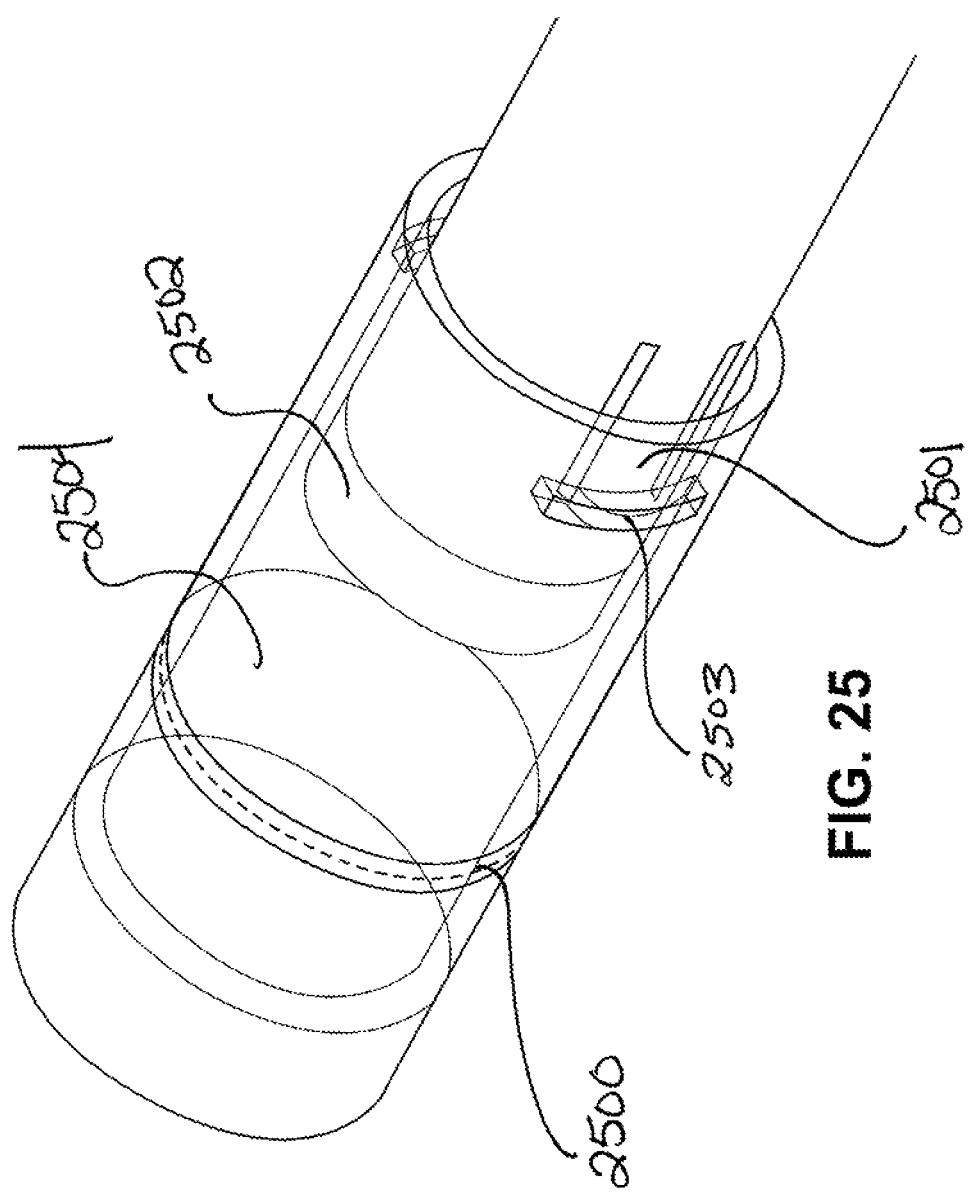

In some embodiments, as shown in FIG. 25, the syringe further includes an additional groove 2500 positioned on the inner surface of the cartridge chamber 2504, distal to the locking mechanism 2501. The groove 2500 is configured to receive the tab 2503 as the second end 2501 reaches the distal end of the cartridge chamber 2504. In some embodiments, the syringe may include a single groove 2500 or multiple grooves 2500 distributed around the circumference of the cartridge chamber 2504. Alternatively, a single groove 2500 may extend around the circumference of the cartridge chamber as shown in FIG. 25. The geometry of the groove 2500 may be configured such that once the groove 2500 receives the tab 2503, the tab 2503 cannot be released from the groove. This prevents the withdrawal of the second end of the cartridge once the flush liquid has been expelled and prevents reuse of the syringe which could be harmful to patients.

Figure 26:
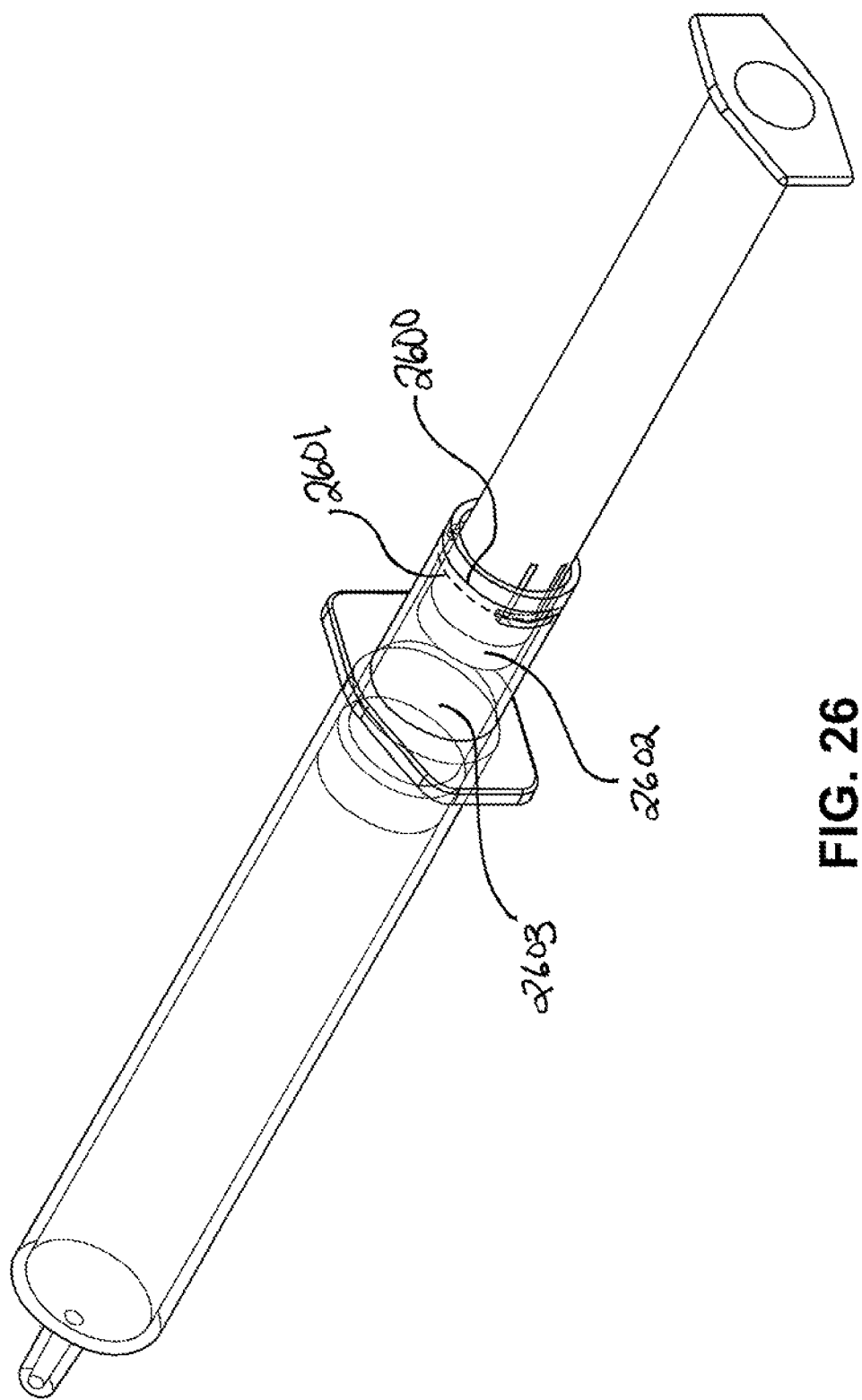

In some embodiments, as shown in FIG. 26, the syringe further includes a first ridge 2600 on the inner surface of the cartridge chamber 2603. The ridge is configured to prevent, the withdrawal of the second end from the cartridge in the proximal direction when the locking mechanism is in the unlocked configuration. In some embodiments, the syringe further includes a second ridge 2601 on the outer surface of the second end 2605 of the cartridge. The first and second ridges are configured such that the first ridge prevents movement of the second ridge in the proximal direction thereby preventing the withdrawal of the second end from the cartridge. The ridges may extend around the circumference of the syringe, as shown, or may only partially extend around the circumference of the syringe. Alternatively, the syringe may include a series of ridges distributed around the circumference of the syringe.

Figure 27:
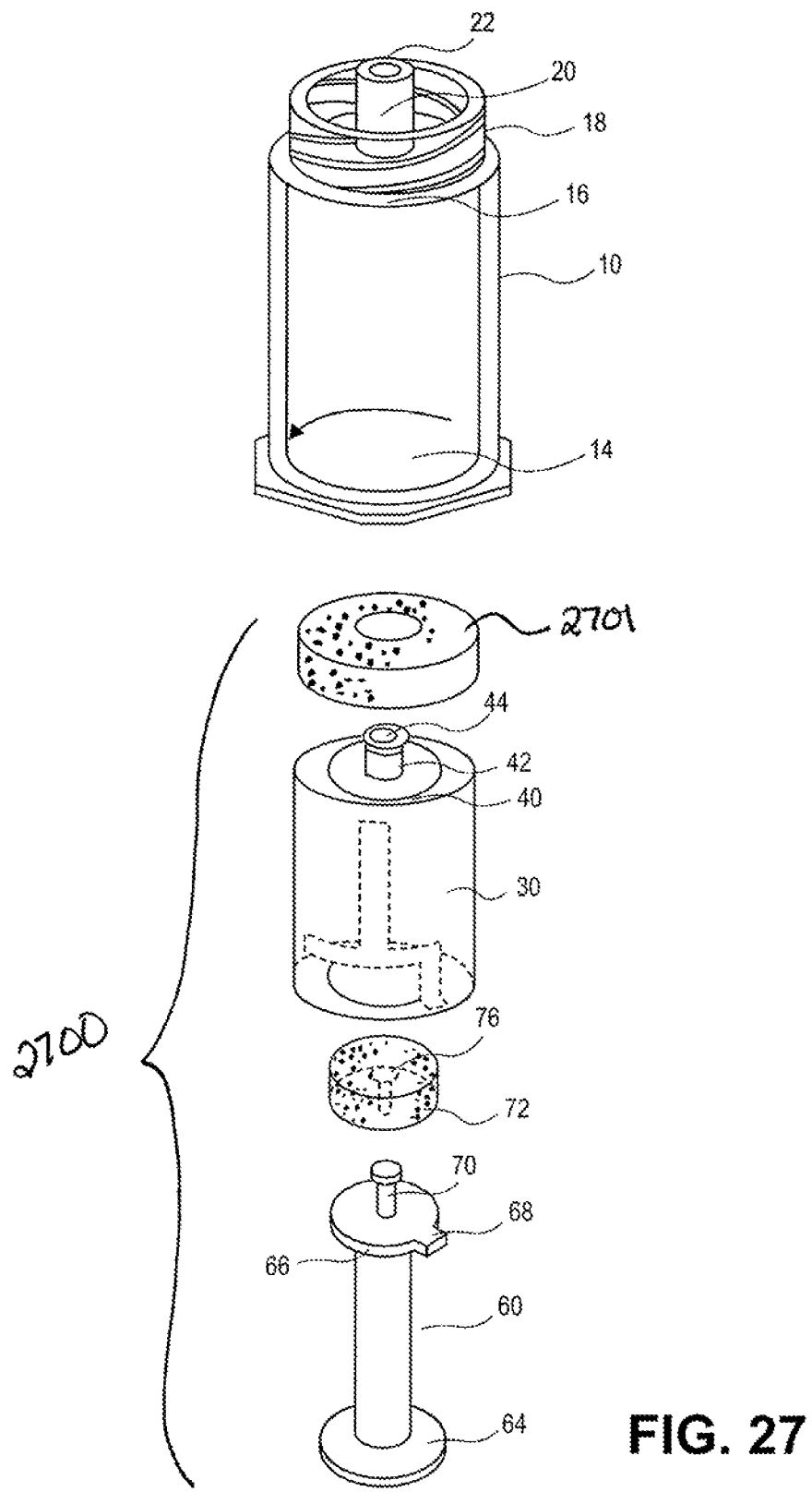
FIGS. 27-28 illustrate various embodiments of a syringe wherein a first end may be fixed with respect to the outer barrel.

The syringe as described above may be configured such that the cartridge is first moved distally within the outer barrel to expel the liquid from the distal chamber, such as medicine. Once the liquid is expelled from the distal chamber, and the cartridge is positioned toward the distal end of the outer barrel, the locking mechanism of the cartridge may be released by rotating the second end of the cartridge with respect to the first end of the cartridge. While the second end is rotated the first end remains fixed with respect to the outer barrel. The first end may be fixed with respect to the outer barrel in one of several variations. In a first variation, as shown in FIG. 27, cartridge 2700 is movable within outer barrel 10. As shown, outer barrel 10 has a non-circular cross section, such as an oval cross section. The inner barrel 30 of cartridge and the first end 2701 of the cartridge have an outer diameter that is also non-circular (e.g. oval) such that the cartridge can be placed within the outer barrel and is movable in the proximal and distal direction within the outer barrel 10. The inner barrel 30 and first end 2701 cannot rotate within the outer barrel 10 due to the non-circular cross sections. As shown, the inner diameter of the inner barrel has a circular cross section. The second end (sealing ring 72 and second piston 60) also has a circular cross section such that the second end can be placed within the inner barrel and is movable in the proximal and distal direction within the inner barrel 30. The second end can rotate within the inner barrel 30 due to the circular cross sections. The second end can therefore be rotated within the inner barrel to unlock the locking mechanism.

Figure 28:
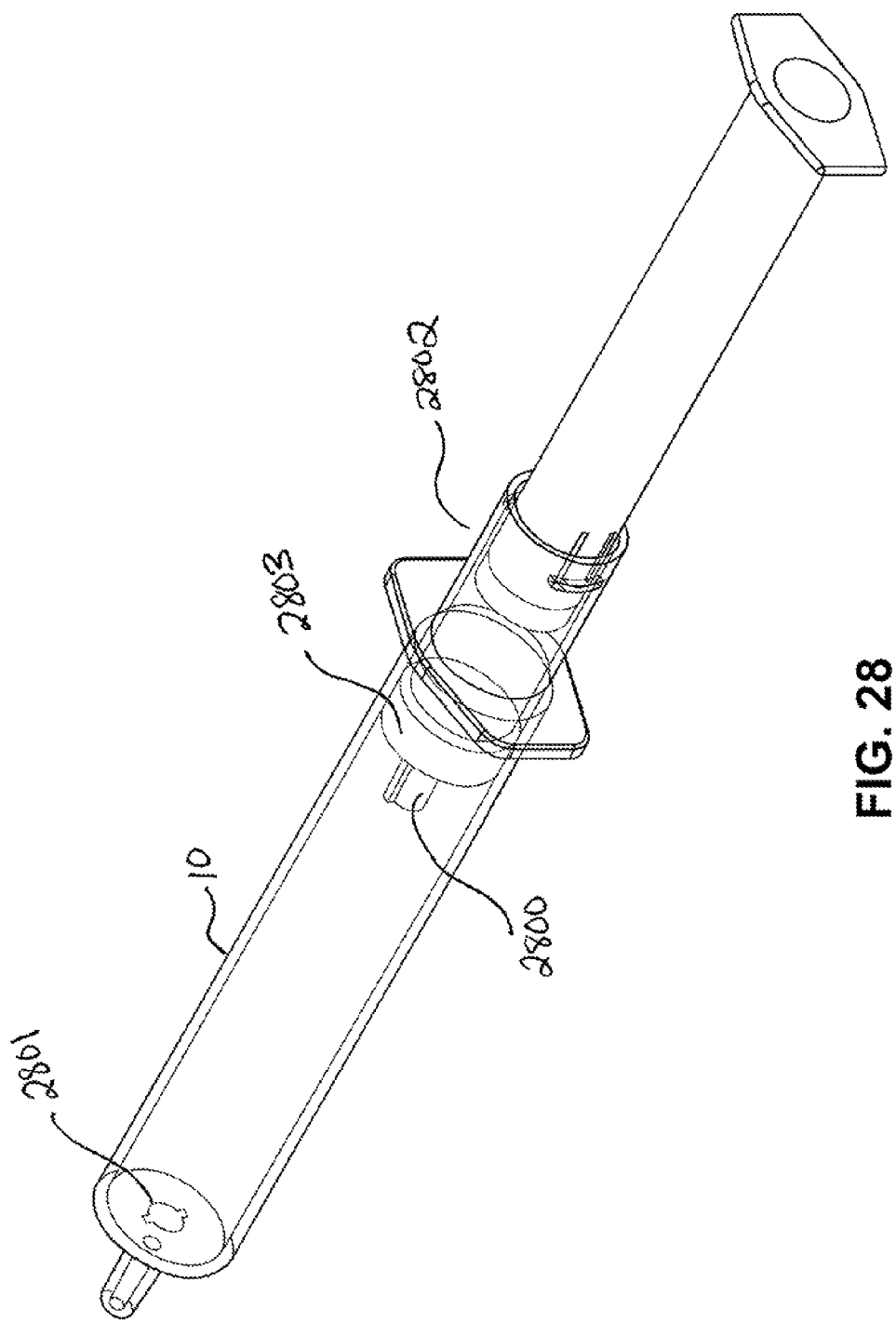

In a second variation, as shown in FIG. 28, the syringe includes a male/female locking mechanism comprising male portion 2800 and female portion 2801. Once the cartridge 2802 is moved distally within the outer barrel 10 to expel the liquid from the distal chamber and the cartridge is positioned toward the distal end of the outer barrel 10, the male portion 2800 (coupled to the first end 2803 of the cartridge) is moved into and received by female portion 2801 (coupled to the distal end of the outer barrel 10). Once the male portion is fitted within the female portion, the male/female locking mechanism prevents rotation of the first end 2803 of the cartridge within the outer barrel 10. Therefore, the locking mechanism of the cartridge may be released by rotating the second end of the cartridge with respect to the first end of the cartridge while the second end is rotated the first end remains fixed with respect to the outer barrel. In a third variation, the syringe may include a screw mechanism, such as a luer lock) such that the first end of the cartridge is screwed into the distal end of the outer barrel and locked into place to prevent further rotation.

In a fourth variation, there may be sufficient friction between the first end of the cartridge and the inner surface of the outer barrel such that as the second end of the cartridge is rotated within the inner barrel, the first end of the cartridge remains fixed. This may be accomplished by having the first end comprise a rubber stopper 72 (as shown in FIG. 1). The friction between the rubber stopper 72 and the inner surface of the outer barrel is sufficiently greater than the friction between the second end of the cartridge and the inner barrel, such that as the second end is rotated, the second end rotates with respect to the inner barrel rather than the first end rotating with respect to the outer barrel.

Figure 29:
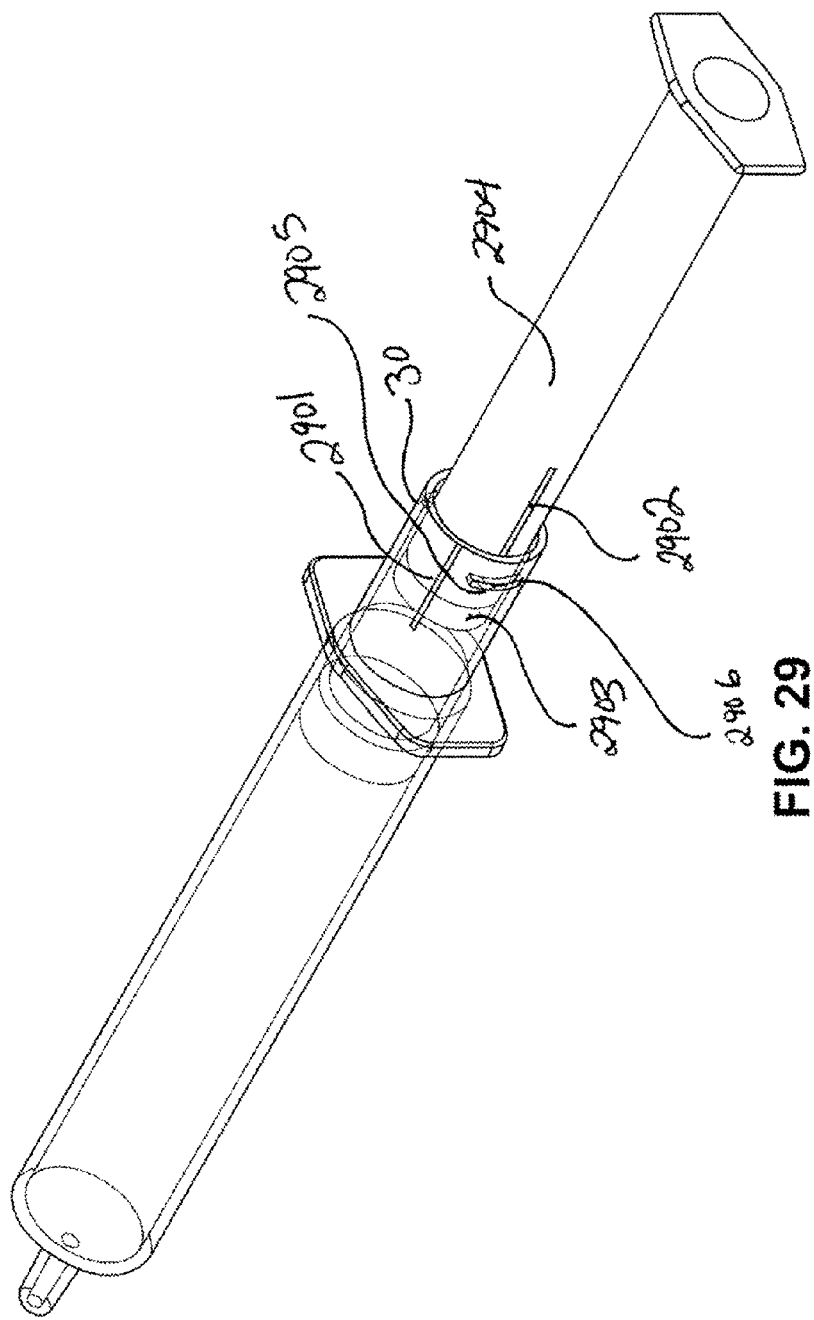
FIG. 29 is a perspective view of an embodiment of a syringe including indicia.

In some embodiments, the syringe may further include lock state indicia that aid a user of the syringe by signifying when the locking mechanism is in the locked configuration and/or when the locking mechanism is in an unlocked configuration. The syringe may also bear a wanting not to prematurely rotate the second end of the cartridge prior to the desired time of expelling the flush liquid, and/or any other suitable indication or warning. The lock state indicia may be printed onto a surface of the syringe or may be printed on a label coupled to the syringe. In the case of a label coupled to the syringe, the outer surface of the syringe may include a groove or recess sized to receive the label. As shown in FIG. 29, the syringe may include lock state indicia 2901 and 2902 that indicate when the locking mechanism is in the locked configuration and the unlocked configuration. As shown, the indicia 2901 (coupled to the inner barrel 30) and 2902 (coupled to the second end 2903 and/or the handle 2904) do not line up when the locking mechanism is locked. As the second end 2903 is rotated and the tab 2905 is released from the groove 2906, indicium 2902 will be moved to line up with indicium 2901 indicating that the locking mechanism is unlocked. As shown, the lock state indicia may be lines or other suitable symbols. The lock state indicia may alternatively include characters or words. For example, indicium 2902 may be the work "LOCKED" while indicium 2901 may be the prefix "UN" such that when the locking mechanism is unlocked and indicium 2901 is aligned with indicium 2902, together they spell the word "UNLOCKED".

Figure 30:
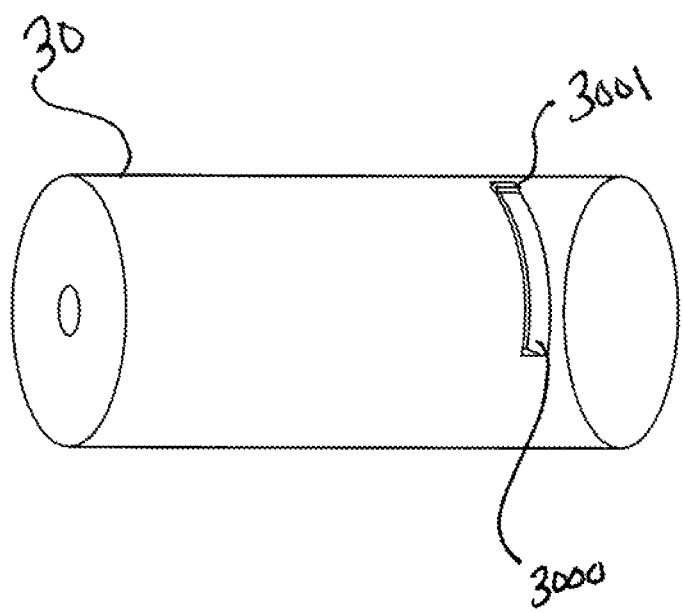
FIG. 30 illustrates a groove of a locking mechanism including a ridge.

In some embodiments, as shown in FIG. 30, groove 3000 coupled to the inner surface of the inner barrel 30 of the cartridge may include a ridge 3001. The ridge 3001 is sized and configured to prevent the tab (not shown) of the locking mechanism from reentering the groove. For example, as shown, tab would be rotated out of groove 3000 by rotating the tab in the counter-clockwise direction (toward the bottom of the Figure). If one were to continue to rotate the tab in the counter-clockwise direction, the tab could reenter the groove from the opposite side, thereby returning the locking mechanism to the locked configuration. In some instances, this may not be desirable and therefore ridge 3001 may function to stop the tab from reentering the groove from that side, thereby maintaining the locking mechanism in the locked configuration.

Figure 31:
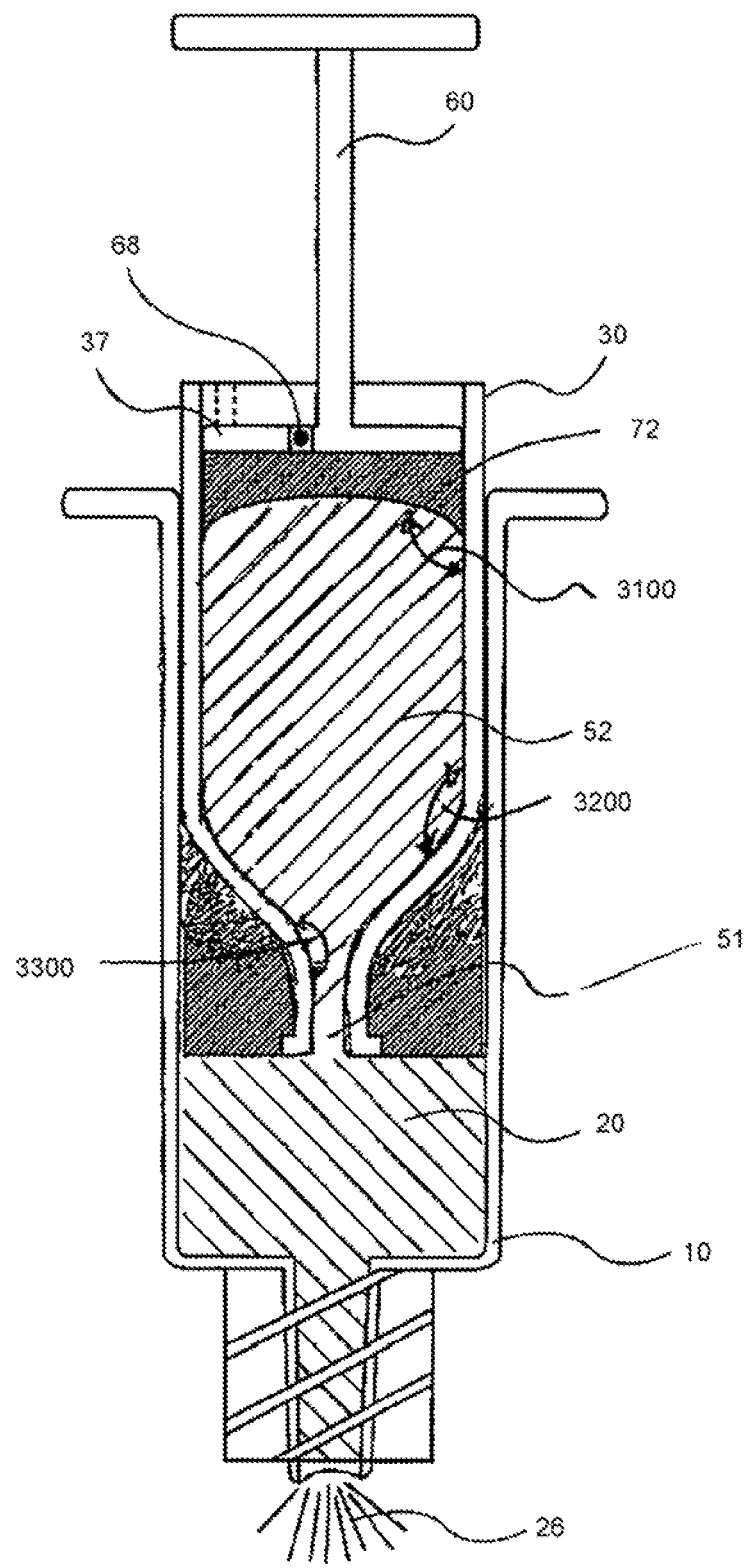
FIG. 31 illustrates a modified syringe having transition angles that reduce the likelihood of the formation of undesired air bubbles within the device.

FIG. 31 illustrates another variation of a modified syringe assembly having features that can be applied to any of the example devices described herein. As noted above, the presence of a fluid or air gap 51 maintains the flushing solution 52 within the cartridge. In some variations it may be important to prevent the occurrence of air bubbles within the cartridge that could interfere with the fluid gap. For example such features can assist in prevention of unintended air bubbles during filling or even after filling of the cartridge with a liquid (in this example a flushing solution 52.) The presence of air bubble can create a risk that a sufficiently large air bubble migrates towards the conduit and join with the fluid gap 51 retained within the conduit causing disruption of the air-fluid interface. To minimize the occurrence of any air bubbles, the syringe and cartridge can be designed with specific transition angles 3100, 3200, and 3300. The transition angles 3100, 3200, and 3300 are respectively: the angle 3100 between a plunger or sealing ring 72 and a wall of the cartridge; the angle between the wall of the cartridge and the bottom of the cartridge 3200; and 3300 the angle between the bottom of the cartridge and the conduit.

In one example, these transition angles can be tailored to prevent formation of air bubbles that would affect the fluid gap 51 in the chamber of the cartridge. For example, making angle 3100 more obtuse than is commonly found in syringes reduces the likelihood of bubble formation at the top of the cartridge. Traditionally this angle is slightly less than 90 degrees in conventional syringes. Additionally, making transition angle 3200 more obtuse than 90 degrees makes bubble formation less likely during filling. Making transition angle 3300 closer to 180 degrees as opposed to a normal 270 degrees) can reduce the likelihood of formation of a bubble. For example, the flush chamber can comprise a tear drop shape where bottoming of the plunger still maintains some fluid in the flush chamber.

One skilled in the art will appreciate that the present invention can be practiced by other than the preferred embodiments, which are presented for purposes of illustration and not of limitation.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A syringe for dispensing a first liquid, the syringe comprising:
   a first chamber having a moveable seal located therein such that movement of the moveable seal changes a volume of the first chamber, the first chamber having an outlet;
   a second chamber movable in the first chamber along with the first chamber movable seal, the second chamber comprising a second movable seal located therein such that movement of the second moveable seal changes a volume of the second chamber;
   a second liquid located in the second chamber, where a volume of the second liquid at least fills the second chamber; and
   a conduit fluidly connecting the first chamber and the second chamber where the conduit contains a fluid gap that is adjacent to the second liquid, where the conduit is configured to retain the fluid gap when the second liquid fills at least the volume of the second chamber, the fluid gap maintains the second liquid in the second chamber;

where the fluid gap is retained in the conduit until the volume of the second chamber changes, such that while the volume of the second chamber remains unchanged volume of the first chamber can be altered by movement of the moveable seal without displacing the fluid gap.

2. The syringe of claim 1, wherein the cartridge comprises about 1 to 10 ml of liquid disposed within the cartridge chamber.

3. The syringe of claim 1, wherein the cartridge comprises about 2 to 3 ml of liquid disposed within the cartridge chamber.

4. The syringe of claim 1, further comprising a second liquid disposed within the first chamber.

5. The syringe of claim 4, further comprising a valve preventing movement of the second liquid into the cartridge chamber.

6. The syringe of claim 5, wherein the volume of the cartridge chamber is constant while the valve is in the closed configuration.

7. The syringe of claim 5, wherein the valve is a one-way valve.

8. The syringe of claim 5, wherein the valve is a duckbill valve.

* * * * *